United States Patent [19]

Conta et al.

[11] Patent Number: 4,603,693

[45] Date of Patent: Aug. 5, 1986

[54] INSTRUMENT FOR CIRCULAR SURGICAL STAPLING OF HOLLOW BODY ORGANS AND DISPOSABLE CARTRIDGE THEREFOR

[75] Inventors: Robert L. Conta; Harvey N. Wallach, both of Trumbull, Conn.

[73] Assignee: United States Surgical Corporation, Norwalk, Conn.

[21] Appl. No.: 328,068

[22] Filed: Dec. 7, 1981

Related U.S. Application Data

[60] Continuation of Ser. No. 138,877, Apr. 10, 1980, abandoned, which is a division of Ser. No. 967,421, Dec. 7, 1978, abandoned, which is a continuation-in-part of Ser. No. 800,965, May 26, 1977, abandoned.

[51] Int. Cl.$^4$ ............................................. A61B 17/11
[52] U.S. Cl. .............................. 128/305; 128/334 R; 227/DIG. 1
[58] Field of Search ..................... 128/334 R, 305; 227/DIG. 1, 19; 206/339

[56] References Cited

U.S. PATENT DOCUMENTS

| | | | |
|---|---|---|---|
| 1,251,258 | 12/1917 | Magill | 128/334 R |
| 2,940,451 | 6/1960 | Vogelfanger et al. | 128/334 R |
| 2,965,900 | 12/1960 | Inokouchi | 227/144 |
| 3,082,426 | 3/1963 | Miles | 128/334 R |
| 3,144,654 | 8/1964 | Malina et al. | 227/19 |
| 3,176,896 | 4/1965 | Mallina | 227/19 |
| 3,191,842 | 6/1965 | Fischer et al. | 227/155 |
| 3,193,165 | 7/1965 | Akhalaya et al. | 227/8 |
| 3,225,996 | 12/1965 | Mallina | 227/137 |
| 3,269,631 | 8/1966 | Takaro | 227/19 X |
| 3,315,863 | 4/1967 | O'Dea | 227/19 |
| 3,388,847 | 6/1968 | Kasulin et al. | 227/19 |
| 3,494,533 | 2/1970 | Green et al. | 227/19 |
| 3,552,626 | 1/1971 | Astafiev et al. | 227/76 |
| 3,593,903 | 7/1971 | Astafiev et al. | 227/76 |
| 3,638,652 | 2/1972 | Kelley | 128/305 |
| 3,836,061 | 1/1974 | Grunwald | 227/155 |

*Primary Examiner*—Michael H. Thaler
*Attorney, Agent, or Firm*—Thomas R. Bremer

[57] ABSTRACT

Apparatus for circular surgical stapling of hollow organs comprising an instrument and disposable cartridge assembly. The instrument comprises a housing with a throughbore in which a tube is received for reciprocation by means of a manually operable squeeze handle. A rod reciprocates within the tube by means of a wing nut cooperating with a threaded part of the rod. A two-part disposable cartridge assembly comprised of an anvil-carrying part and a staple-carrying part are detachably mounted on the rod and housing, respectively. Keys are provided to hold the anvil-carrying part and the staple-carrying part in rotational orientation relative to the rod. Mutually coacting stops on the tube and rod determine the extent of reciprocation which is variable in dependence upon the position of the rod which, in turn, is dependent upon the juxtaposition of the anvil-carrying part with the staple-carrying part when the apparatus is closed on tissue preparatory to effecting a circular anastomoses. A novel geometric configuration for the anvil-carrying part is provided for easy removal of the instrument from a stapled anastomosis. Further, the interior of the stapling mechanism is generously vented to prevent the build up of excessive pressure in tissue confined within the stapling mechanism.

5 Claims, 78 Drawing Figures

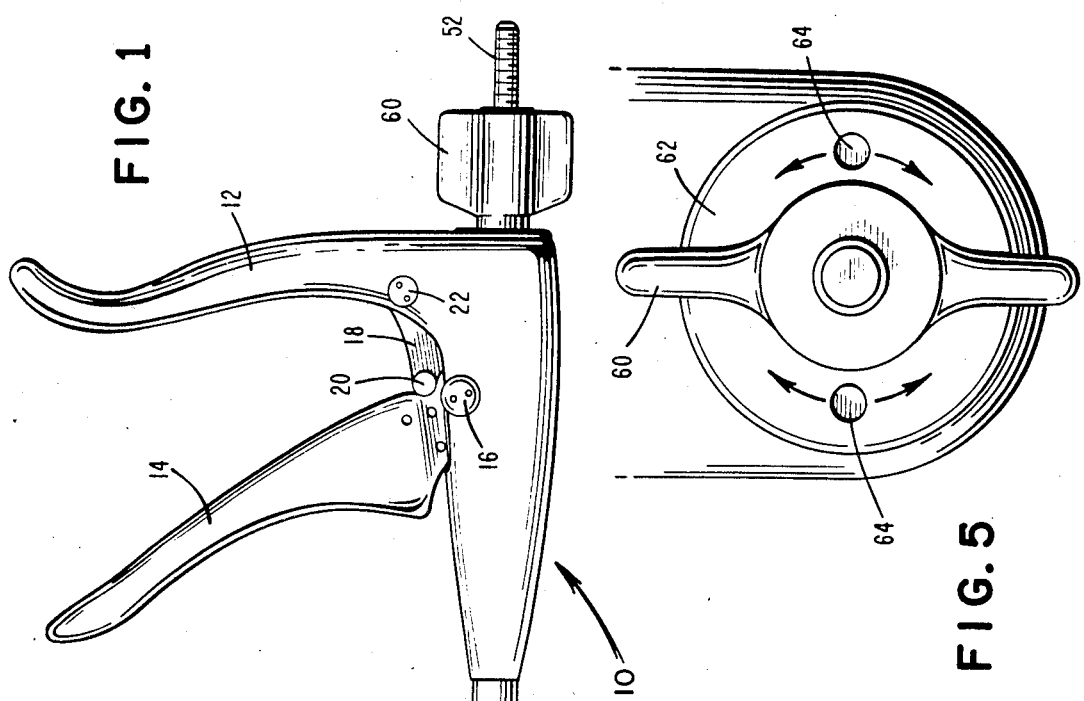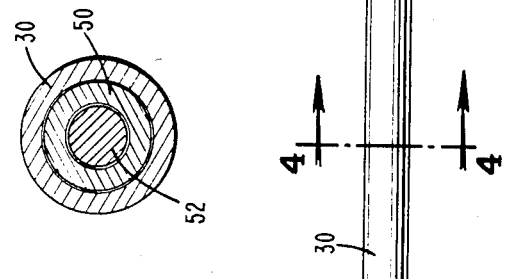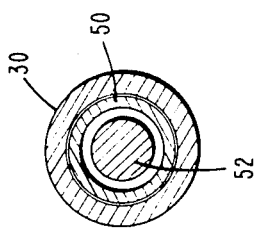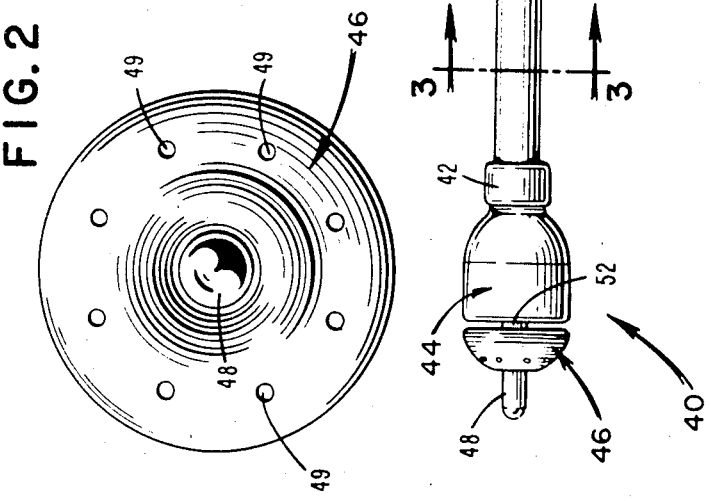

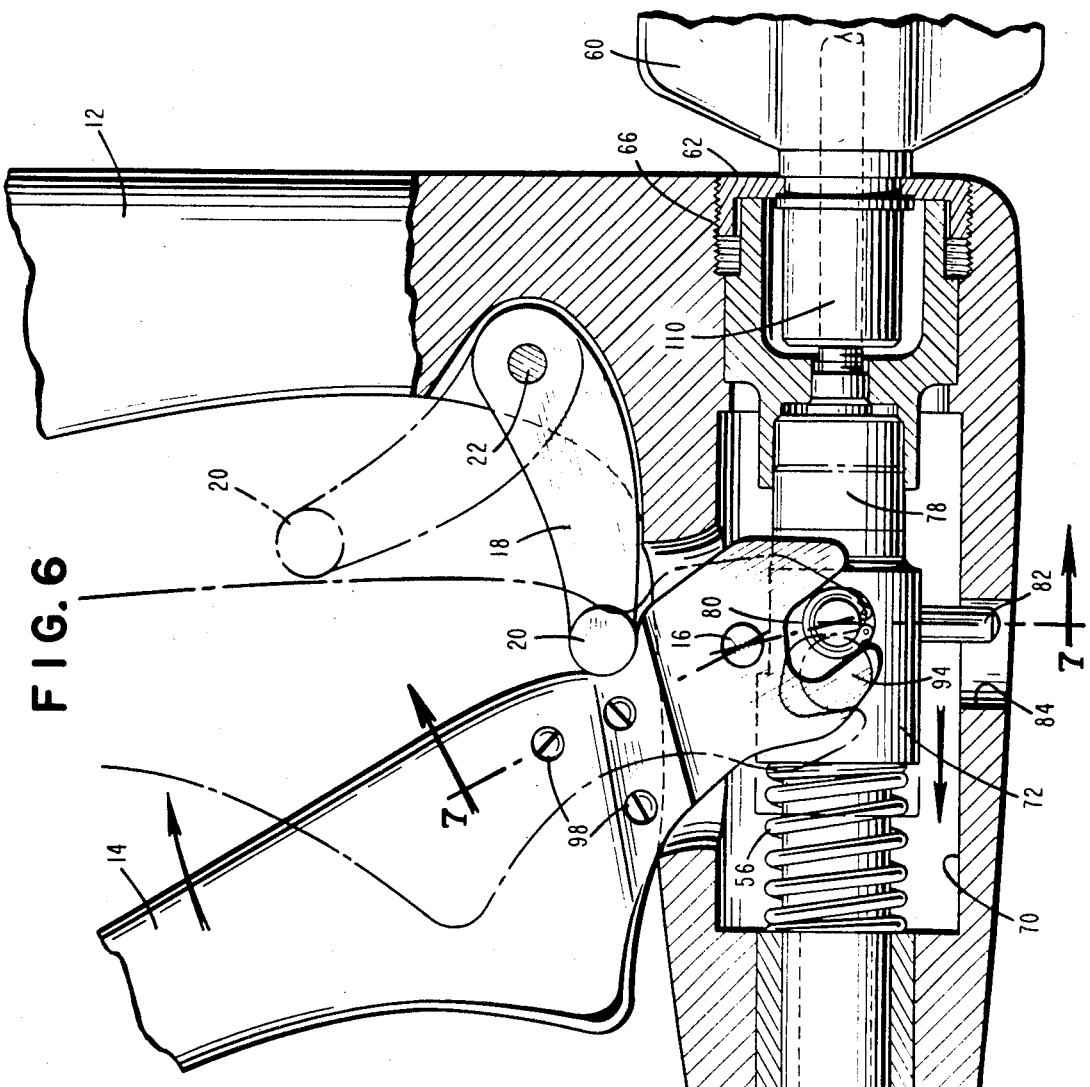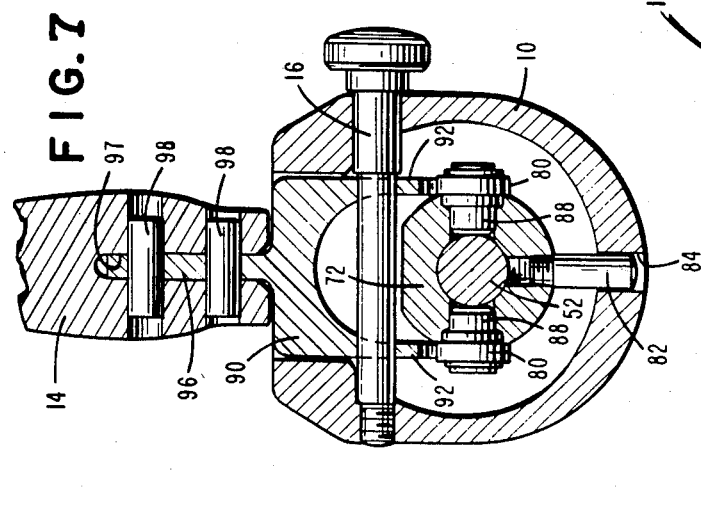

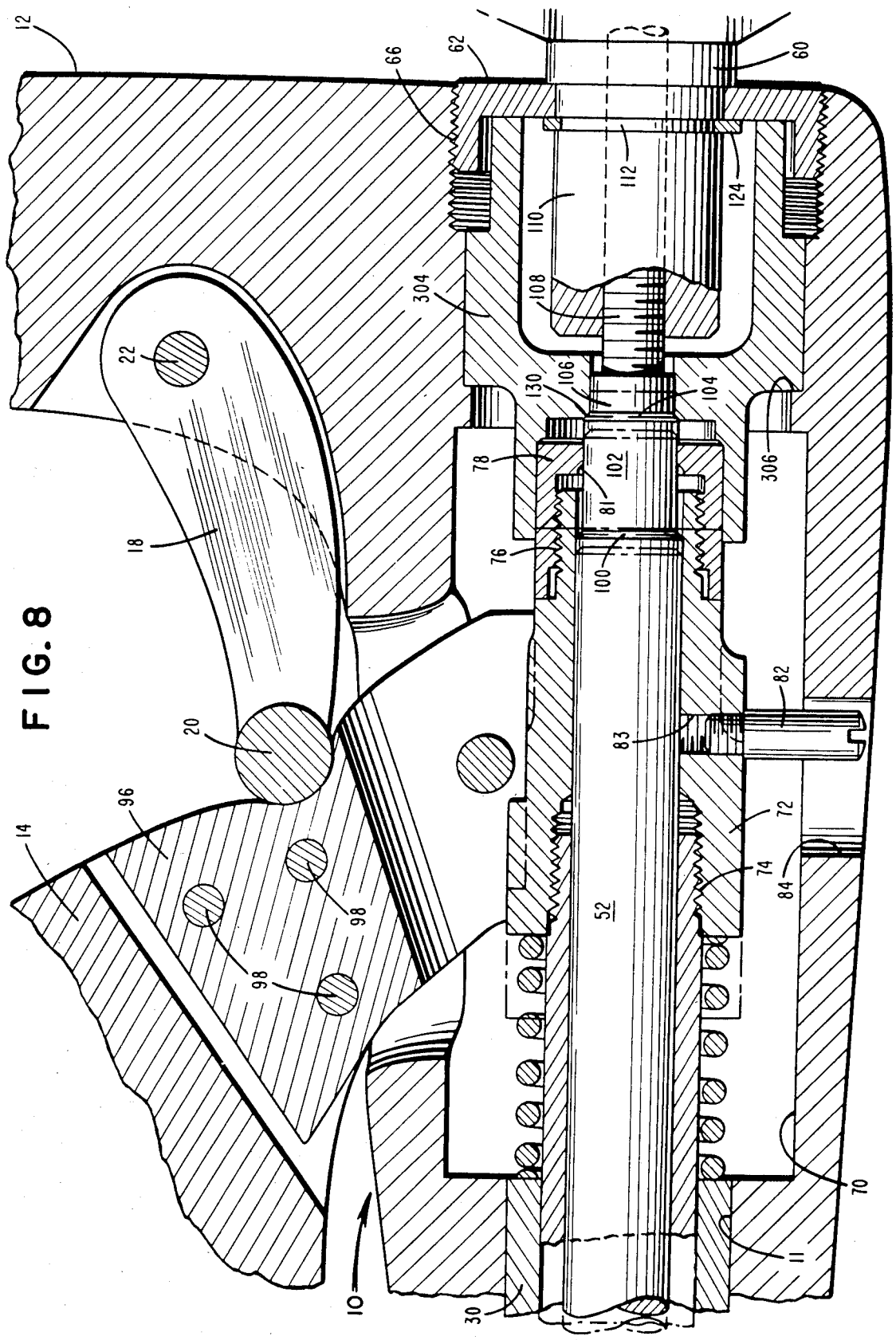

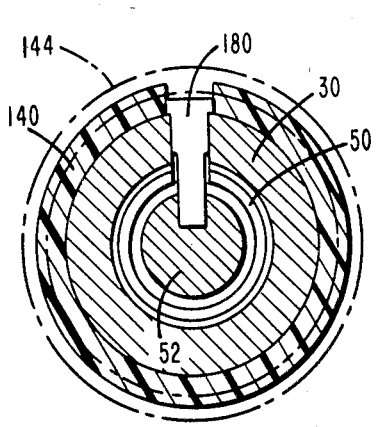
FIG. 11
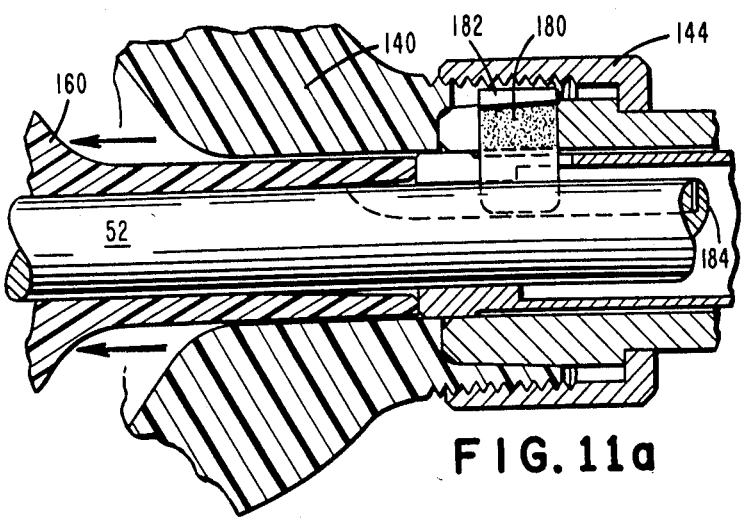
FIG. 11a
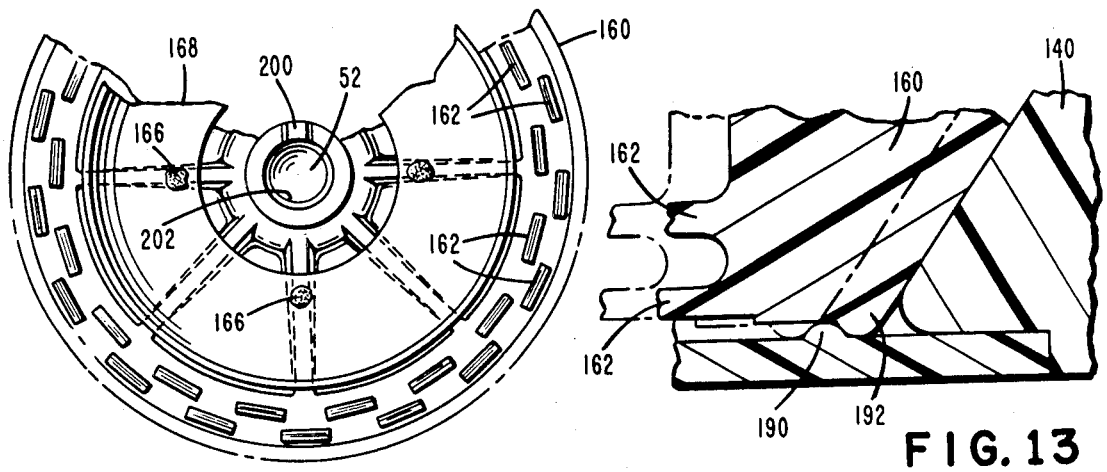
FIG. 12
FIG. 13
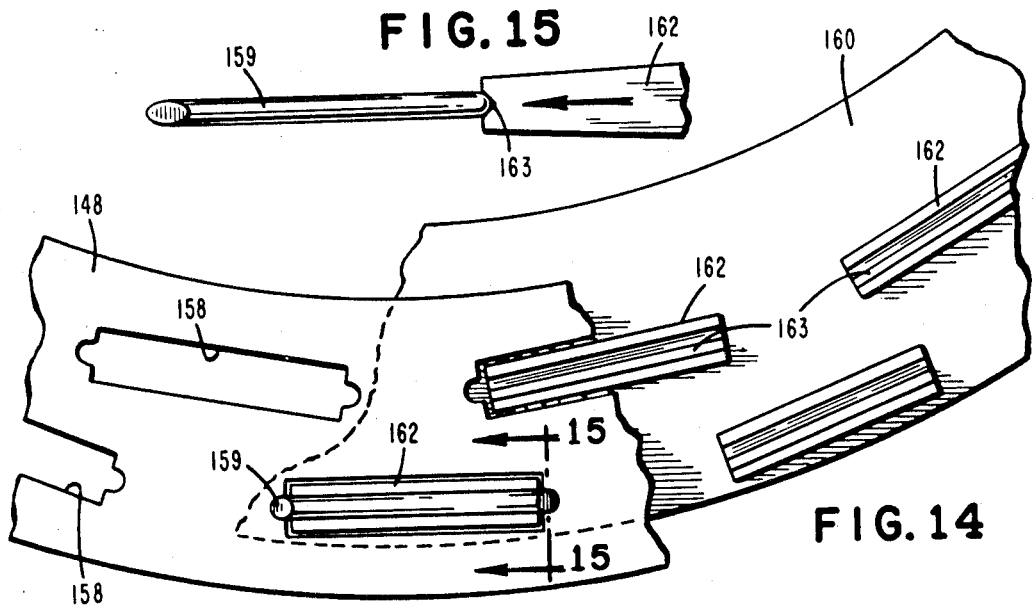
FIG. 15
FIG. 14

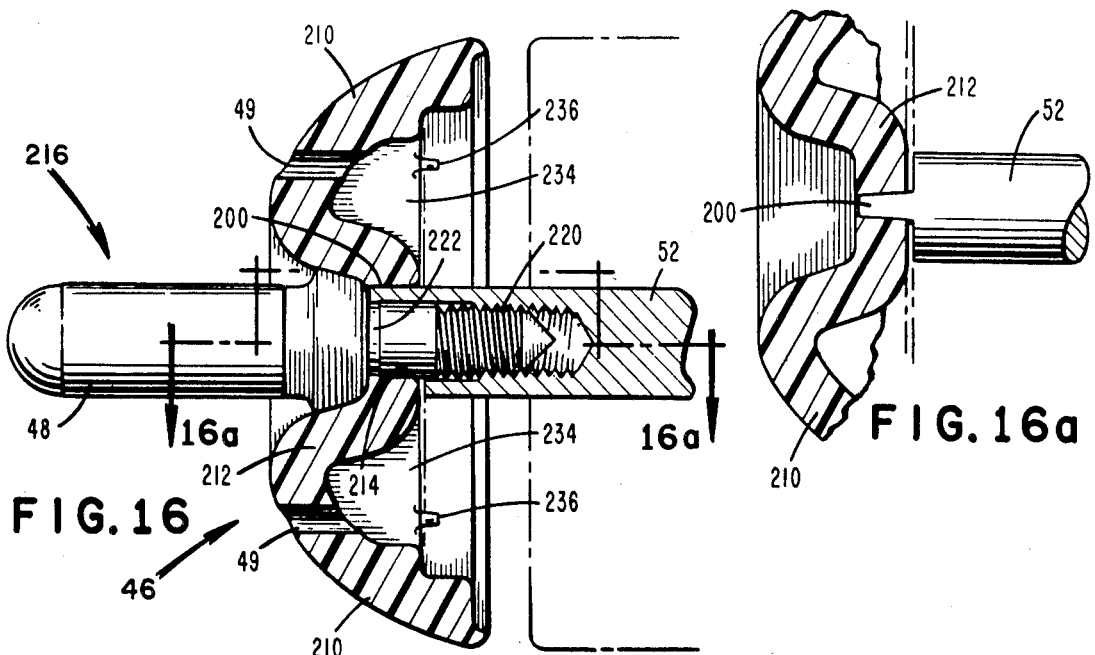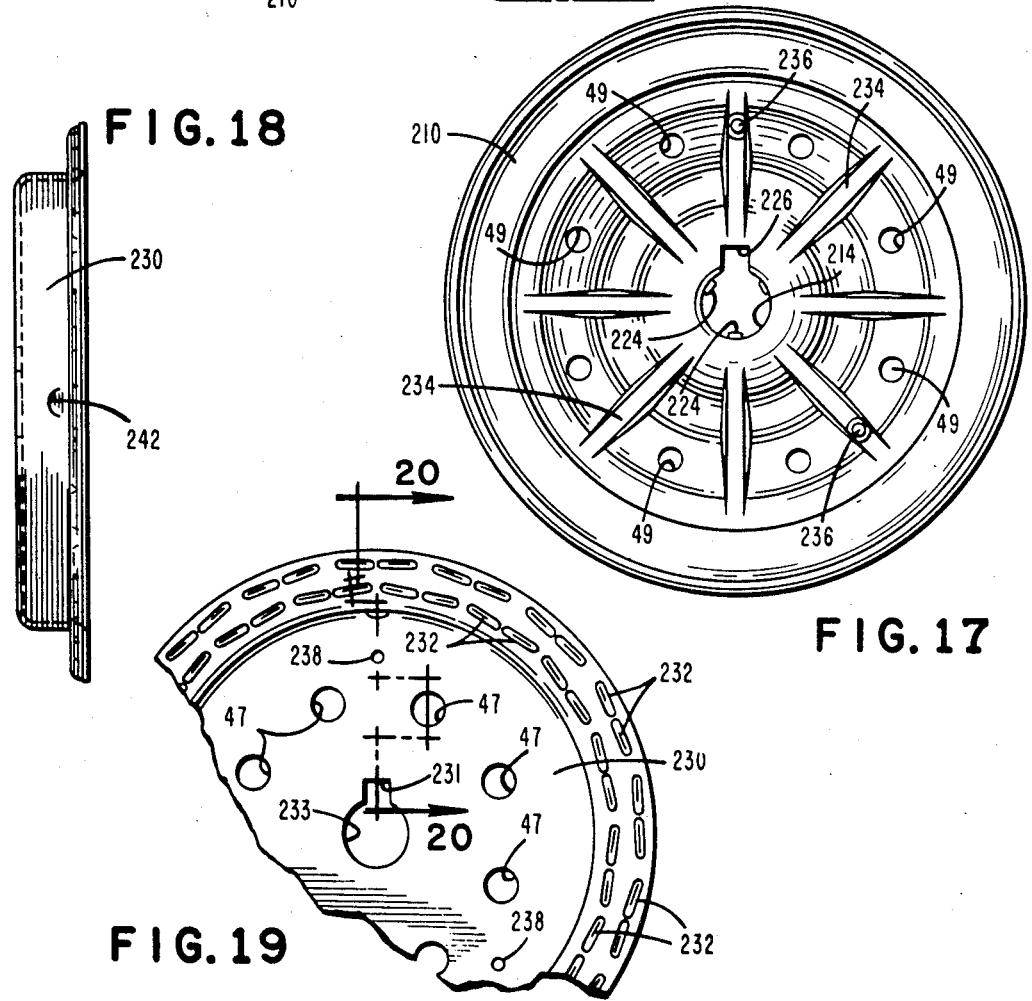

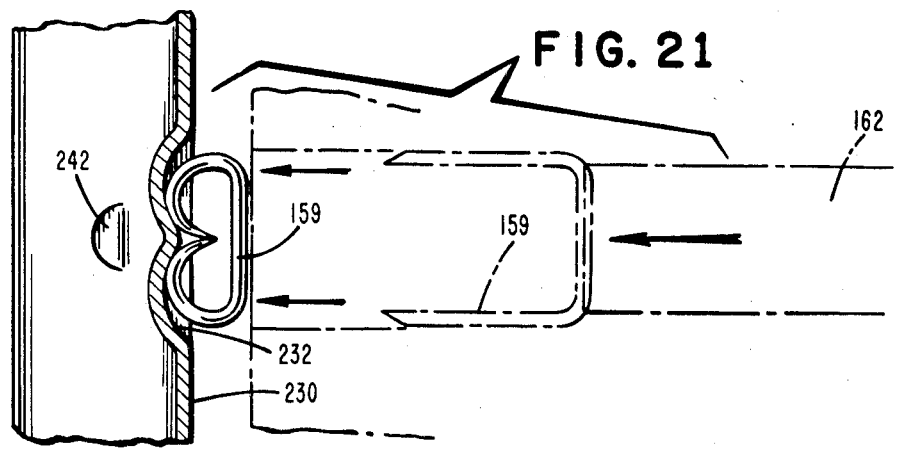
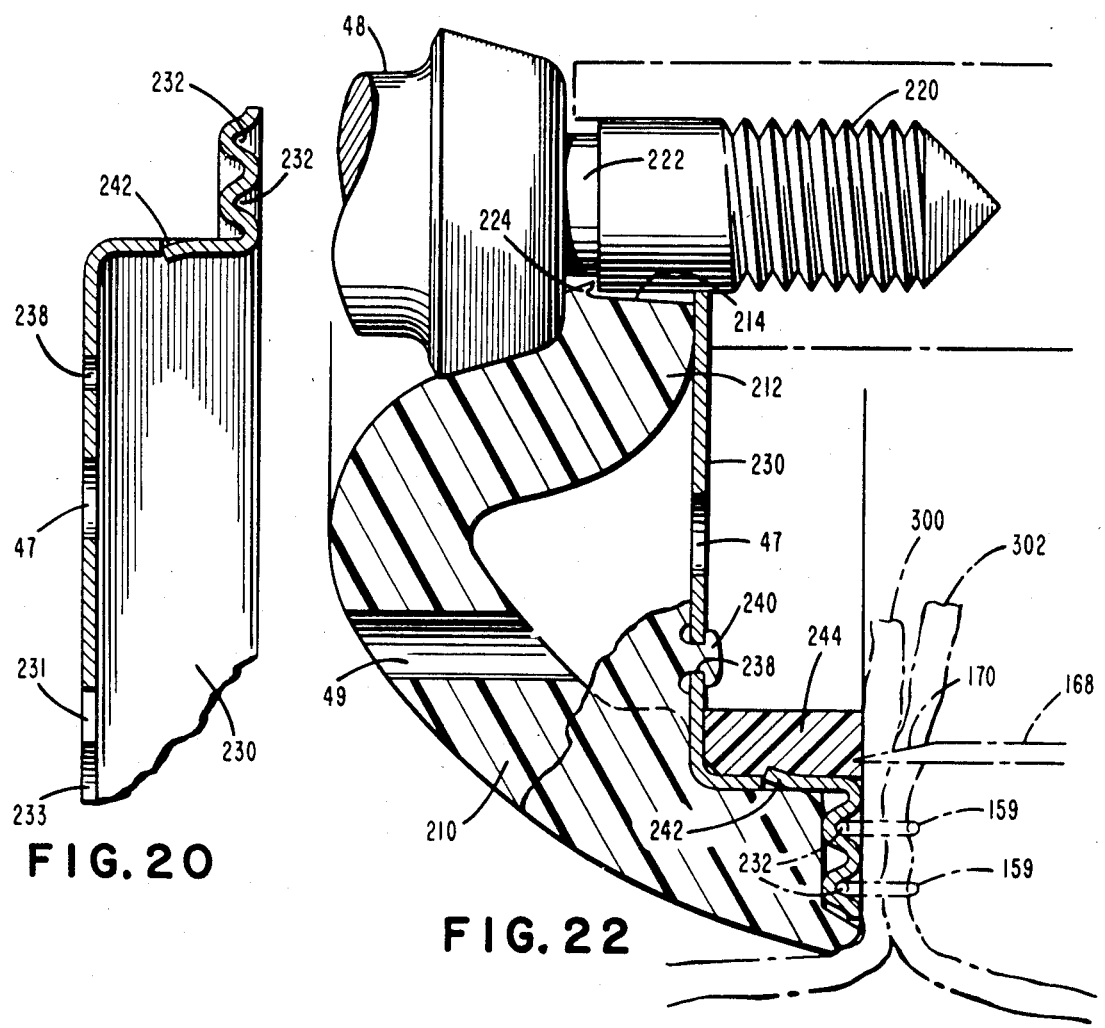
FIG. 20
FIG. 22

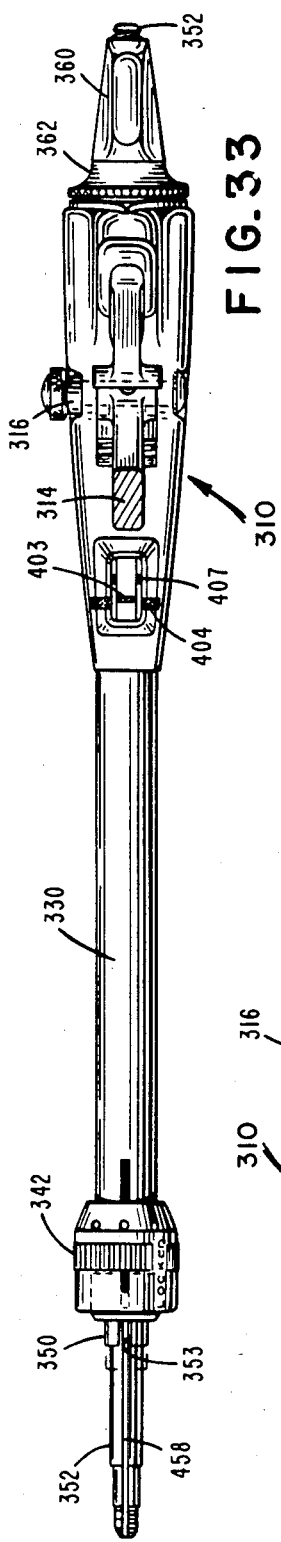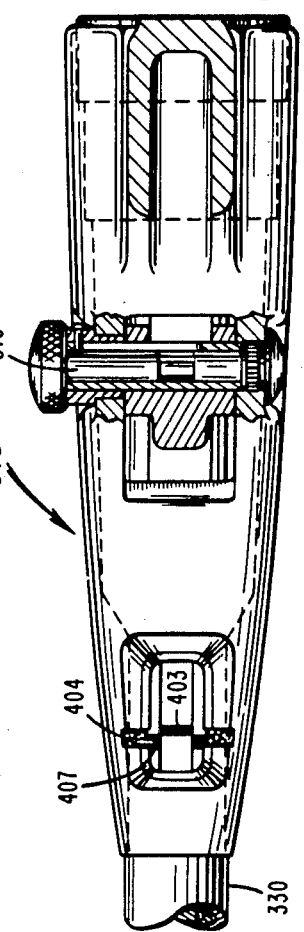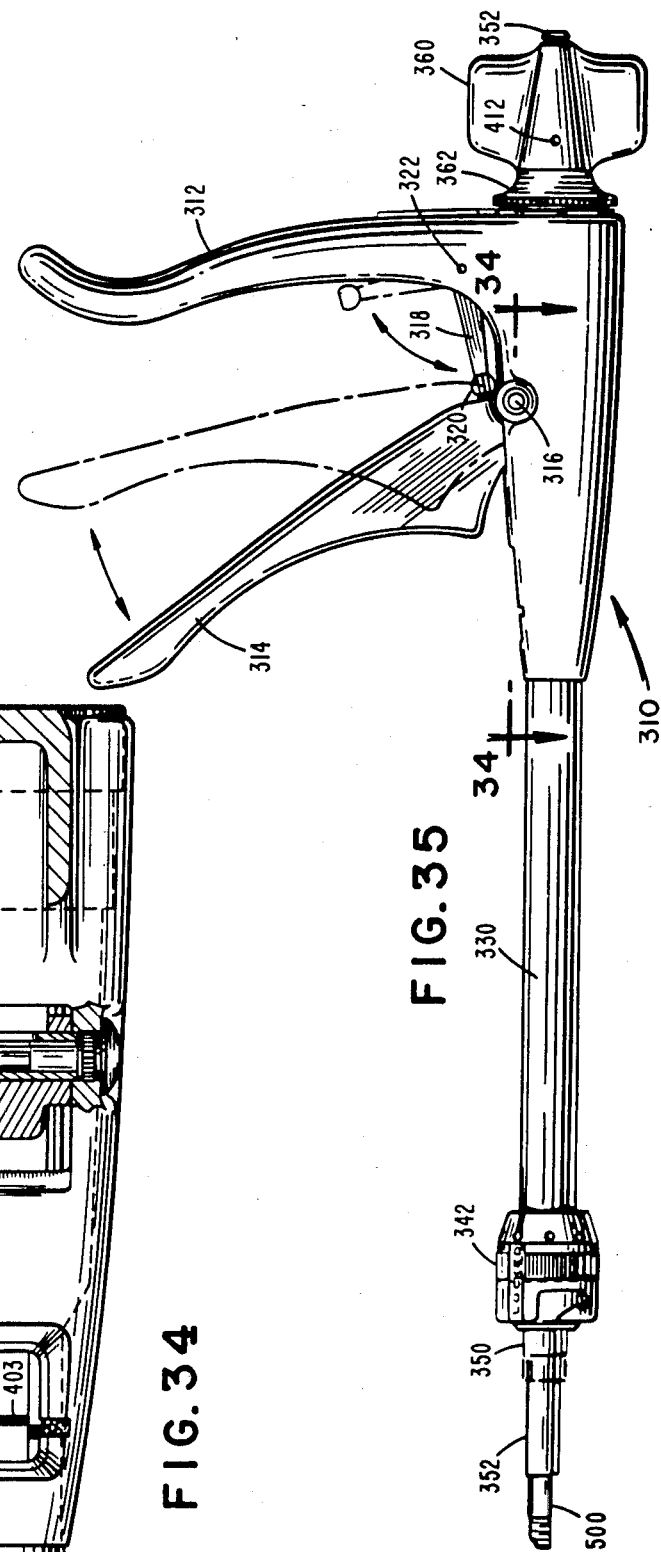

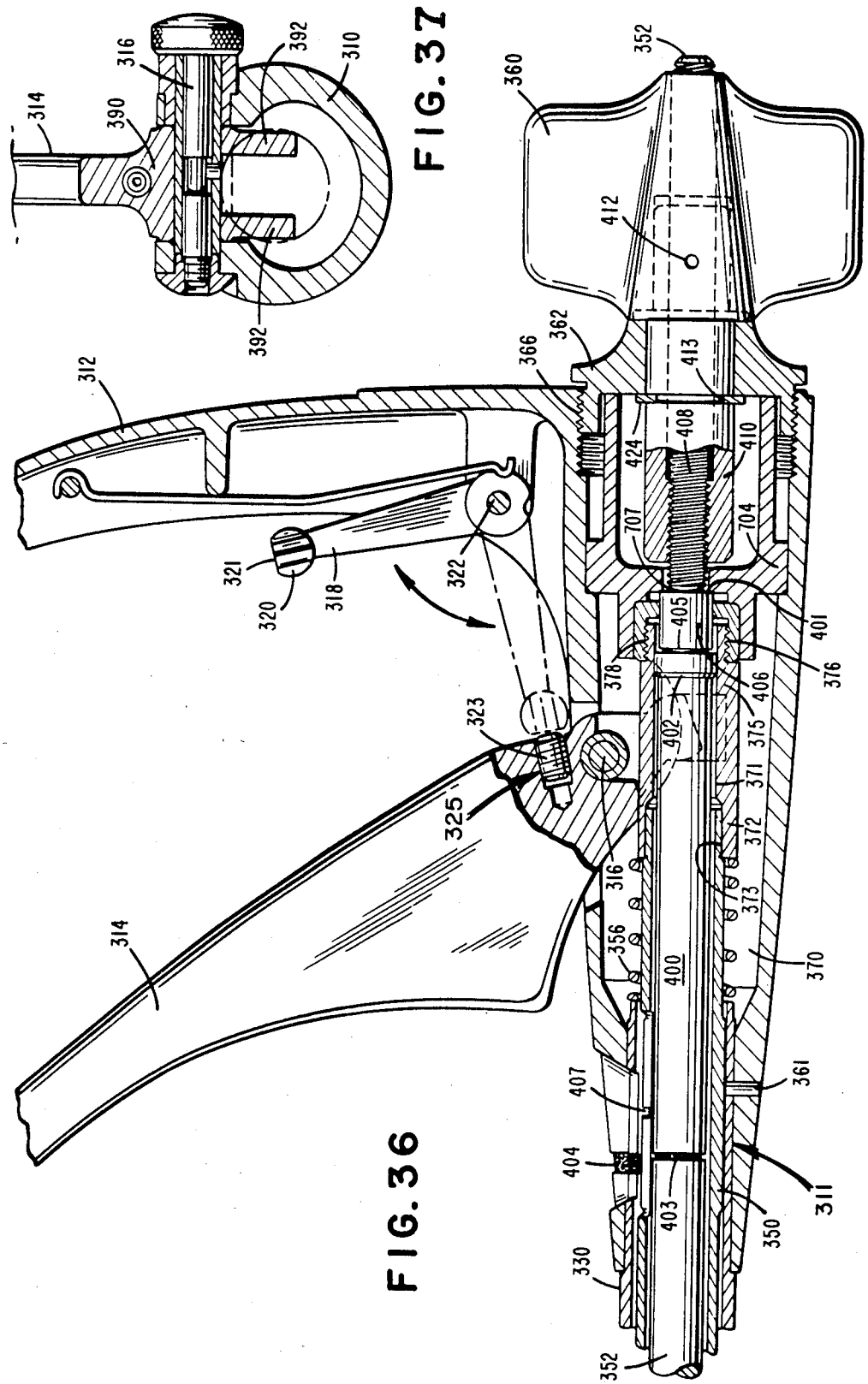

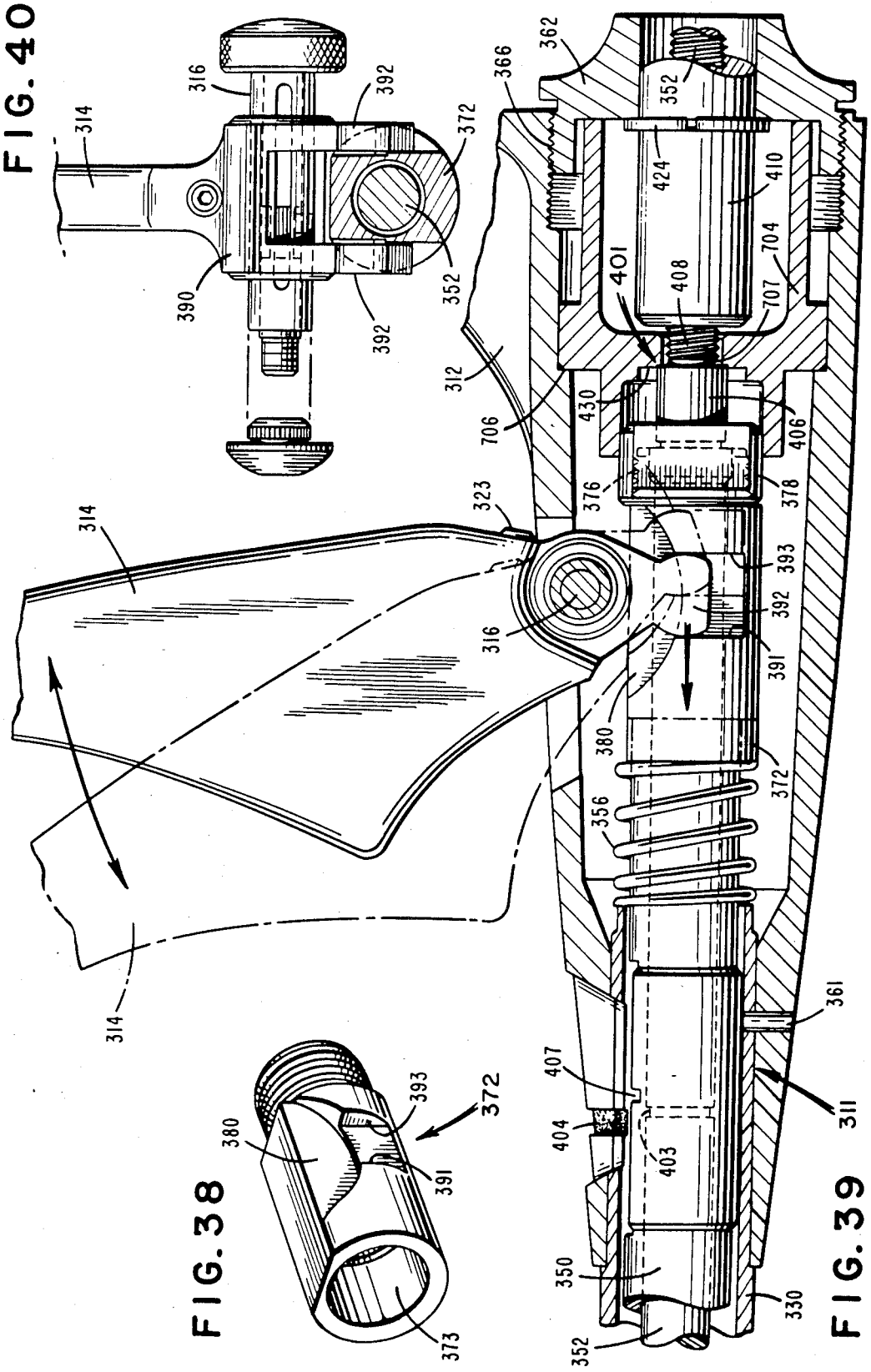

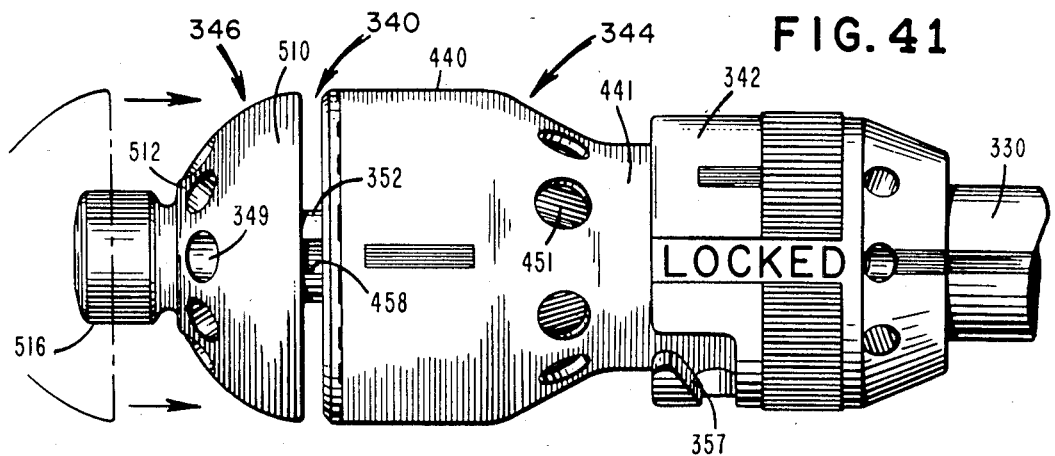
FIG. 41
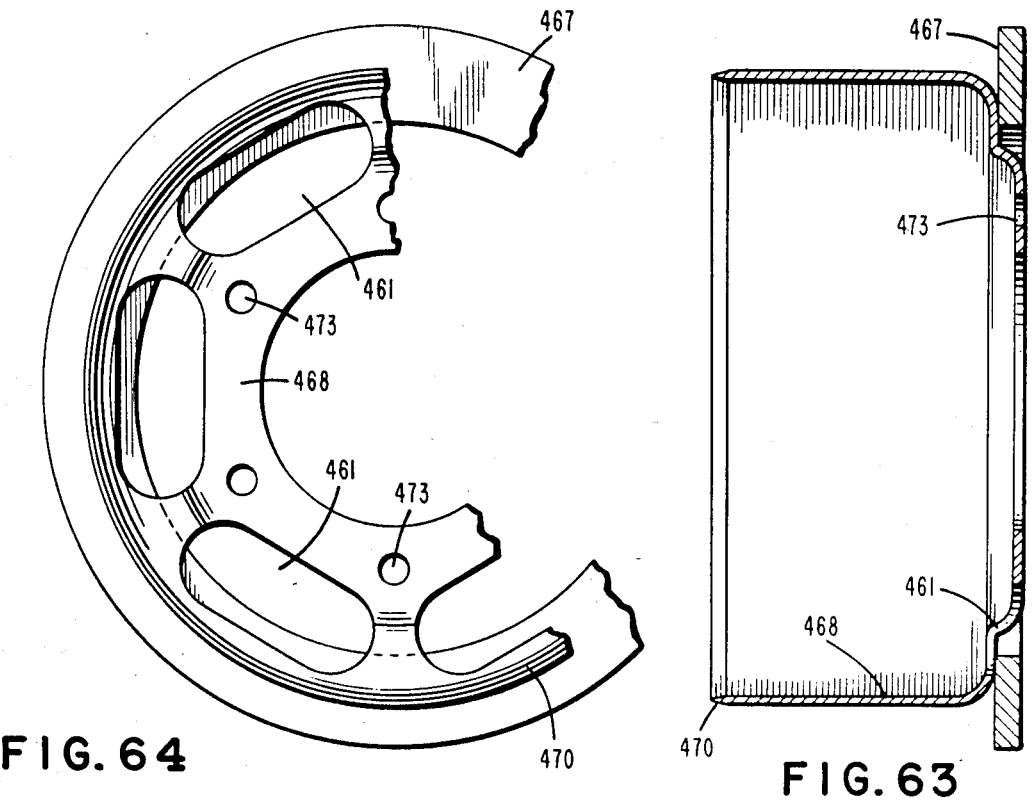
FIG. 64
FIG. 63
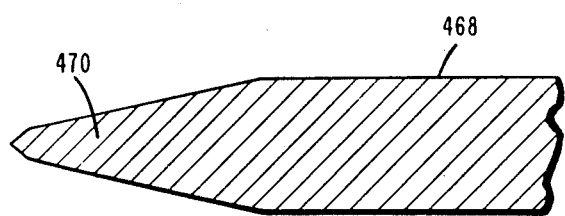
FIG. 65

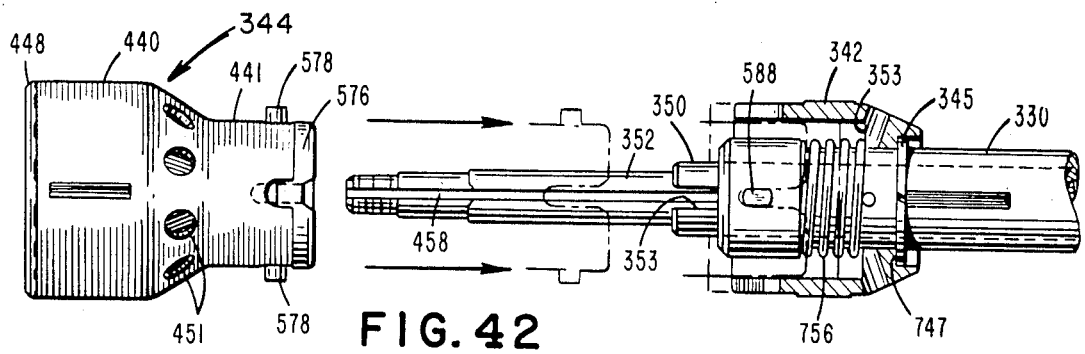
FIG. 42
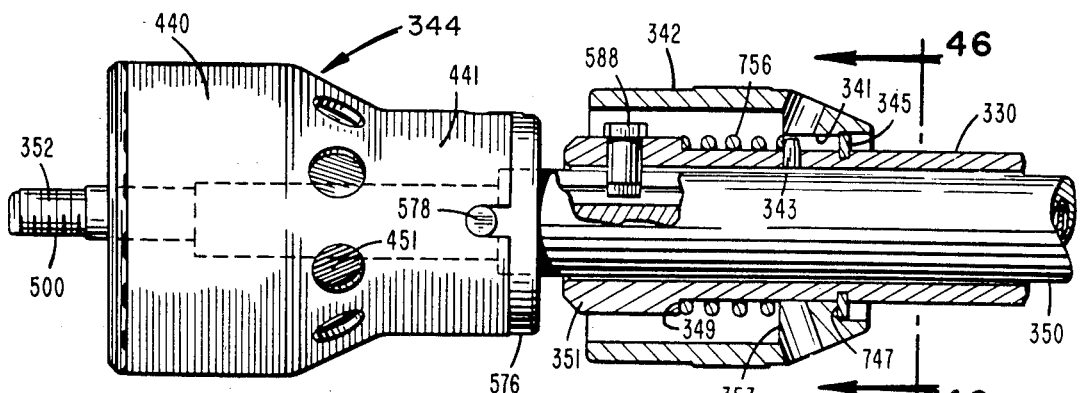
FIG. 43
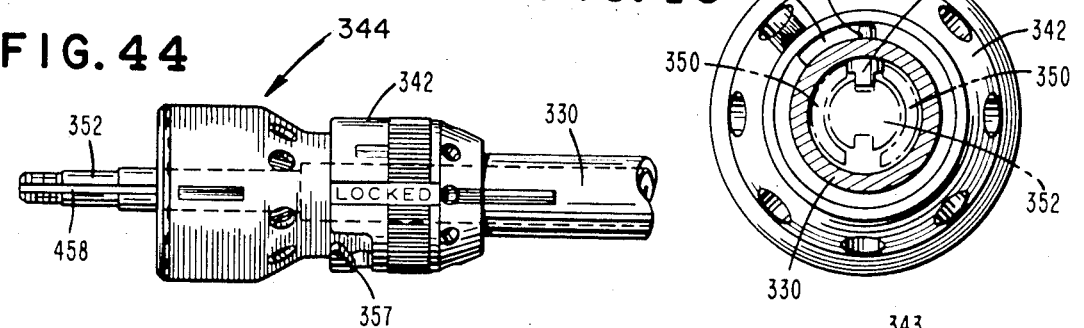
FIG. 46
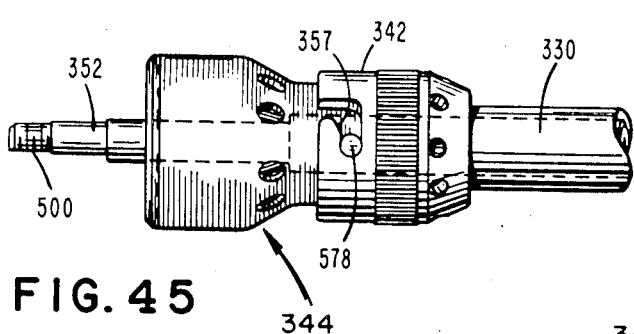
FIG. 44
FIG. 45
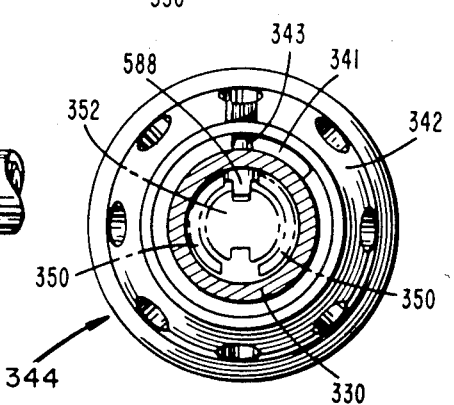
FIG. 47

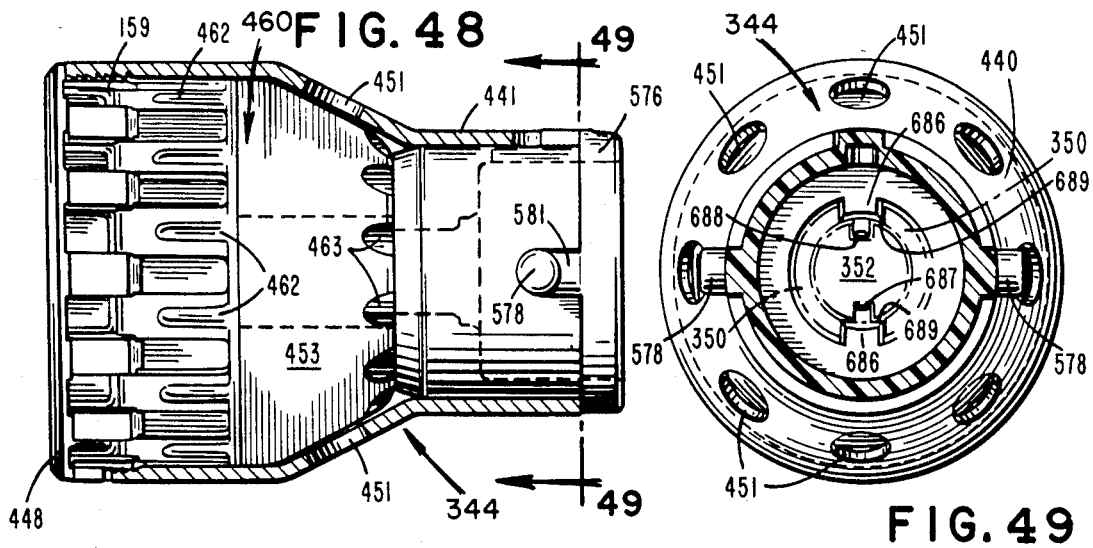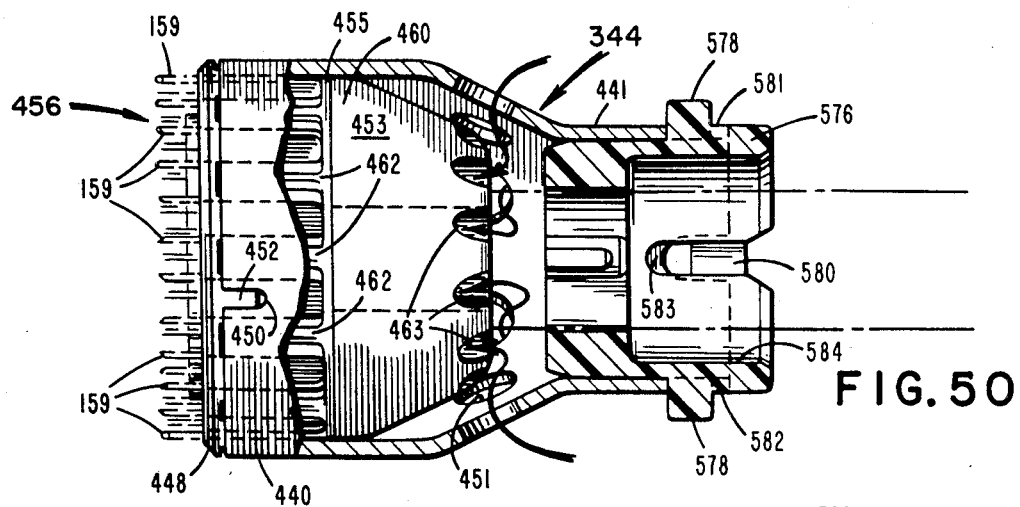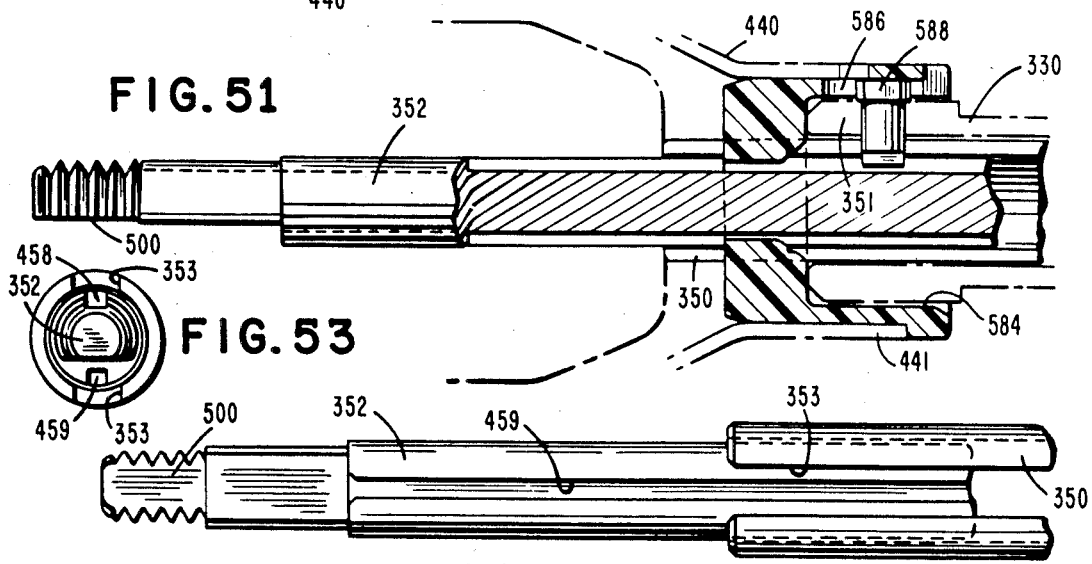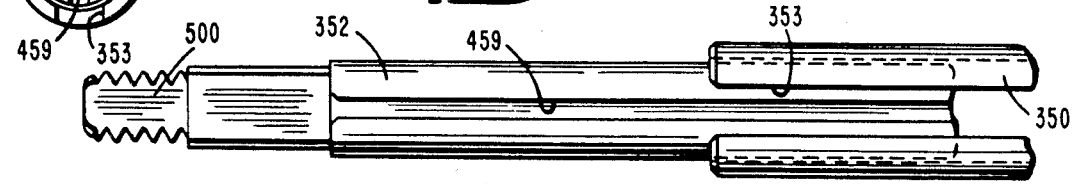

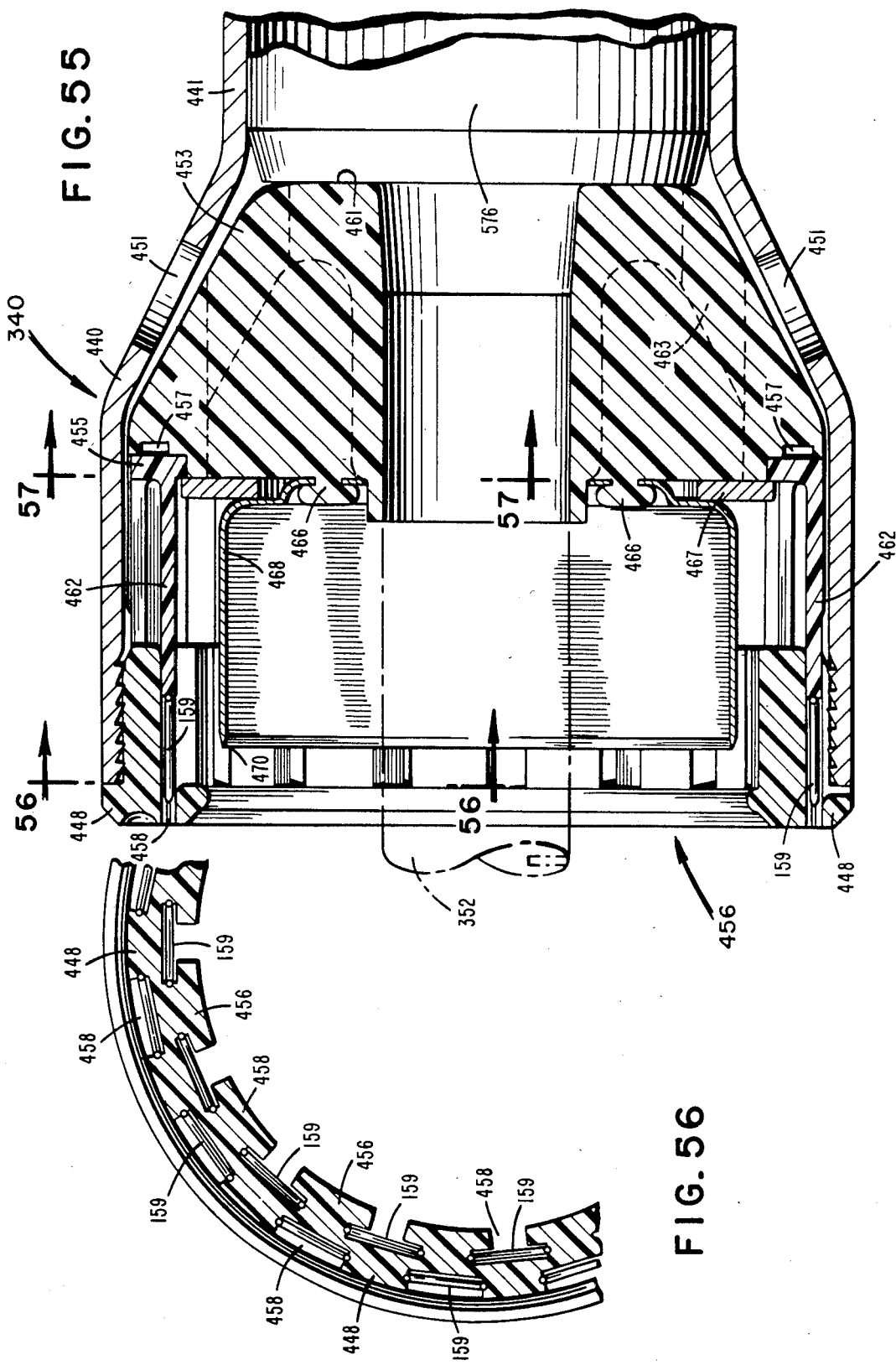

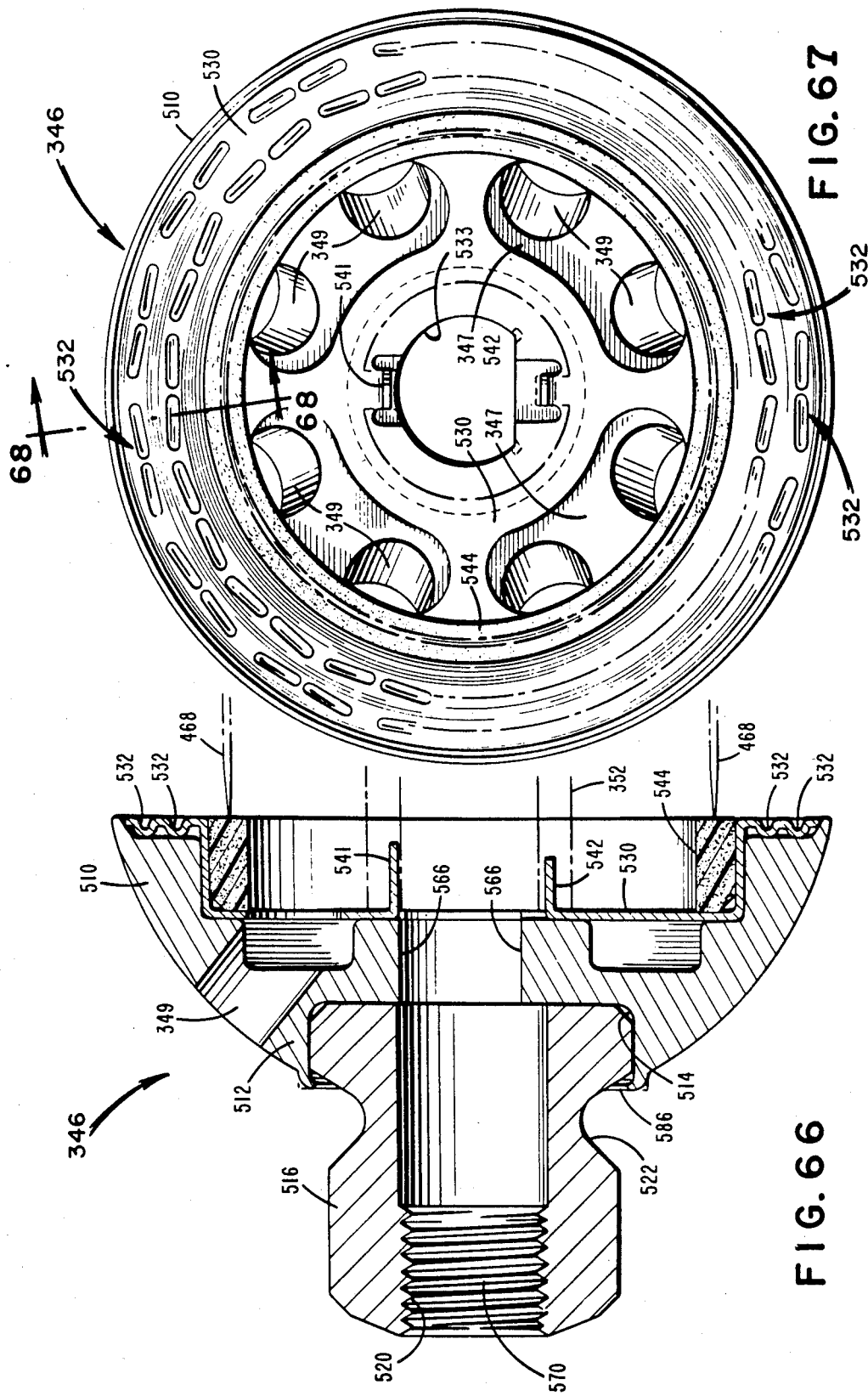

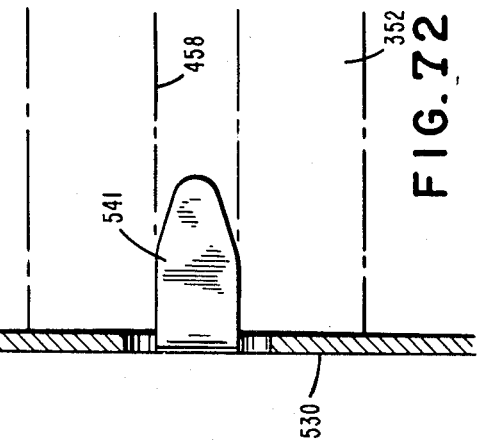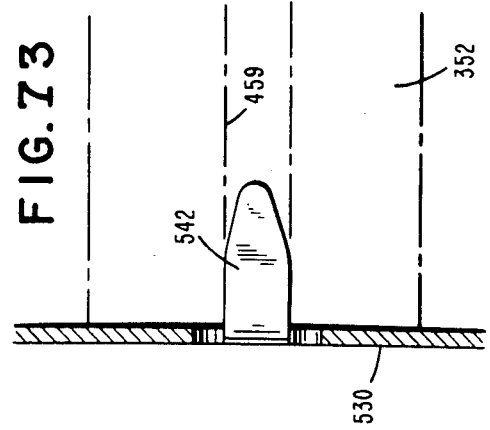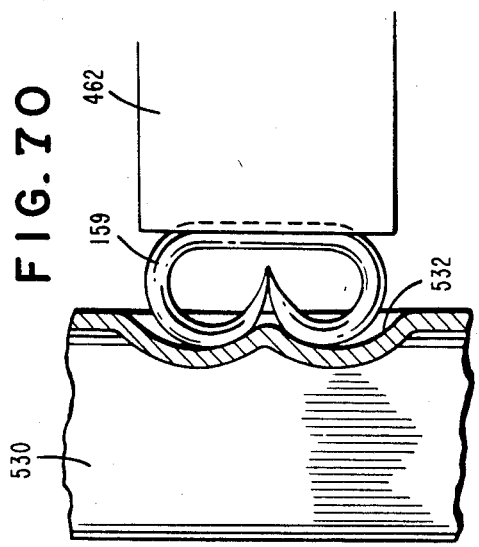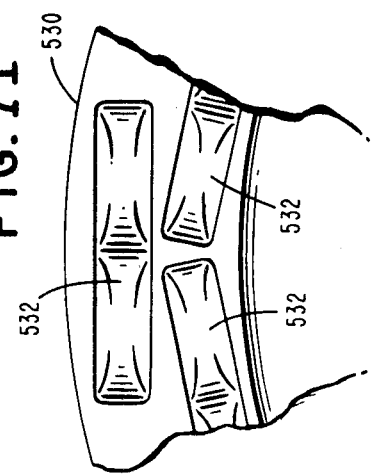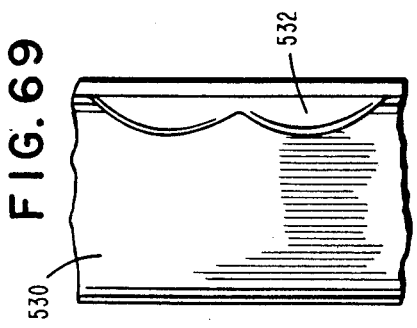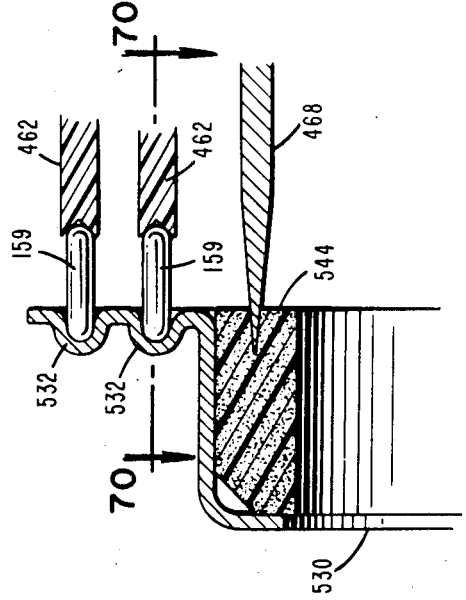

INSTRUMENT FOR CIRCULAR SURGICAL STAPLING OF HOLLOW BODY ORGANS AND DISPOSABLE CARTRIDGE THEREFOR

RELATED U.S. APPLICATION DATA

This is a continuation of application Ser. No. 138,877, filed Apr. 10, 1980, abandoned, which is a division of application Ser. No. 967,421, filed Dec. 7, 1978, abandoned, which is a continuation-in-part of U.S. patent application Ser. No. 800,965, filed May 26, 1977, abandoned.

BACKGROUND OF THE INVENTION

1. Field of the Invention

This invention relates to an instrument for circular surgical stapling of hollow body organs and more particularly, to an instrument for effecting end-to-end, side-to-side, and side-to-end anastomoses and a disposable cartridge therefor.

2. Description of the Prior Art

Presently in the prior art, several instruments are known for circular joining by staples of hollow body organs. U.S. Pat. Nos. 3,638,652, 3,552,626, 3,388,487 and 3,193,165 all relate to instruments of this type, which are useful in surgical procedures involving the colon and the esophagus. Despite the fact that these instruments are known in the prior art, they have never been introduced into clinical use in the United States. These instruments, which are disclosed in the aforementioned patents, have the important drawback of requiring hand loading of the suturing staples into the staple magazine of the instrument after each use of the instrument. This means that once the instrument is actuated and its staples ejected and clinched, it must then be cleaned before the magazine can be manually refilled with staples. While being refilled, the instrument, of course, is inoperative and may not be further used in the on-going surgical operation. The aforementioned U.S. Pat. No. 3,552,626 discloses a form of the instrument in which the staple magazine and associated anvil of the instrument are interchangeable so that different sizes may be mounted on the same instrument body, but this arrangement is solely for the purpose of accommodating hollow body organs of different sizes.

SUMMARY OF THE INVENTION

The present invention is directed to an instrument of the type generally described and was developed to overcome the drawbacks and disadvantages which one experiences when attempting to use similar instruments according to prior art teachings and, most notably, those teachings which are contained in the aforementioned patents. One of the principal benefits results from providing the staple carrying cartridge part and the staple clinching anvil part as disposable elements and, thus, the staple forming parts, which are subject to wear from usage and/or damage from cleaning and storage, are furnished as new parts for each stapling procedure. The parts most likely to wear or damage are the pusher fingers, which eject the staples from the cartridge and the anvil, against which the staple legs are clinched or formed. Additionally, successive uses of an instrument during a surgical procedure are easily attained simply by detaching a spent cartridge and replacing with a fresh cartridge. Keying of the parts of the disposable cartridge to each other and to the body of the instrument is also a feature of the invention to insure that all parts are in the correct orientation and properly indexed; hence, when the instrument is actuated, the staples are ejected through the tissue of the hollow body organ and clinched to effect the desired staple line.

The present invention provides an instrument for effecting end-to-end anastomoses, side-to-side anastomoses, or end-to-side anastomoses by means of a pair of concentric circles of staples to ensure a high margin of security in maintaining the desired tissue joining. The present invention, further provides a unique disposable cartridge, and a precise cooperation between the cartridge, the anvil and the instrument for staple forming alignment. Variations in staple dimensions and array patterns are easily provided by a variety of cartridge designs. Unique provision is made for easy removal of the instrument from the stapled anastomosis. Further, the interior of the stapling mechanism is generously vented to prevent the build up of excessive pressure in the tissue confined within the stapling mechanism while the tissue is being compressed and clamped prior to and during the actual firing of the staples and the excision of the excess tissue in the lumen of the anastomosis.

To our knowledge, the instruments of the prior art have had only limited experimental use on animals in the United States. Our experience in such use of these instruments has revealed several areas of inadequacy. Specifically, a hazard lies in employing a single circular row of staples. The failure of a single staple to form and close properly can cause a leak in an anastomosis staple line. The consequences of such a leak can be fatal to the patient. There is also a problem associated with the removal of the instrument from the anastomotic circular staple pattern. In the most frequent applications for an instrument of this type, the staple forming elements on one side of the anastomosis, for instance, the anvil assembly, must be removed by passing then through the inner diameter or lumen of the newly formed circular staple line. A solution to the one problem of staple line security creates a characteristic which increases the other problem. That is, the addition of a second inner concentric row of staples for greater security of the staple forming line creates a smaller lumen than would an anastomosis with a single circular row of staples. Therefore subsequent removal of part of the instrument through the lumen becomes more difficult. The prior art does not address this problem. The present invention overcomes this problem by providing the anvil portion with a particular geometry which permits the anvil side of the stapling mechanism to be readily removed through the lumen of the circular stapled anastomosis.

Another problem is associated with the amount of body tissue which must be gathered within the inner row of staples to insure that all staples pass through the walls of the ends of the hollow organs being anastomosed. Some amount of excess tissue must be gathered within the inner row of staples to ensure that all free edges are caught within the inner circular staple pattern. As the stapling elements are closed to clamp the tissue prior to and during stapling, and as the pusher and knife assembly advance to staple and cut away excess tissue, the excess tissue is confined in a progressively smaller volume. In prior art instruments, this progressive confinement of excess tissue often created compressive pressures of sufficient magnitude to interfere with the stapling and cutting functions. That is, in some instances, the compressed confined tissue extrudes outward through the clamped circular stapling area with enough force to deflect the knife blade and the staples as they progressed through the tissue. Obviously any such deflection greatly reduces the reliability of the stapling and cutting system.

BRIEF DESCRIPTION OF THE SEVERAL VIEWS OF THE DRAWINGS

Further advantages and details of the present invention will become more evident from a consideration of the following descriptive text, when taken in conjunction with the appended drawings in which:

FIG. 1 is a view in side elevation showing the novel instrument assembled with a disposable cartridge;

FIG. 2 is an end view of the disposable cartridge illustrated in FIG. 1;

FIG. 3 is a sectional view taken along line 3—3 of FIG. 1;

FIG. 4 is a sectional view taken along line 4—4 of FIG. 1;

FIG. 5 is an end view of the instrument looking at the adjustable wing nut;

FIG. 6 is a view partly in section through the main body of the instrument showing the manner in which the instrument is assembled and the handle is manipulated to cause the reciprocating motion of the driver;

FIG. 7 is a sectional view of FIG. 6 taken along line 7—7;

FIG. 8 is a view in section through the body of the instrument showing the stop arrangement in detail;

FIG. 11 is a view in section taken along line 11—11 of FIG. 10;

FIG. 11a is a view in section through the keying arrangement illustrating positions following staple ejection;

FIG. 12 is a front end view of the staple carrying part of the disposable cartridge showing the pusher and knife;

FIG. 13 is a detailed section showing safety detent arrangement;

FIG. 14 is a front end view showing the pusher and staple guide;

FIG. 15 is a side elevational view showing coaction between staple and pusher;

FIG. 16 is a side view, partly in section showing the anvil part of the disposable cartridge;

FIG. 16a is a top view in section along line 16a–16a of FIG. 16;

FIG. 17 is a view of FIG. 16, with the anvil removed;

FIG. 18 is a side elevational view of the anvil;

FIG. 19 is an elevational view of the anvil;

FIG. 20 is a view in section through the anvil;

FIG. 21 is a view in section through the anvil illustrating the manner in which a staple is clinched; and FIG. 22 is a view in section through the anvil part of the disposable cartridge showing the staple line and knife cutting of tissue.

FIG. 33 is a top plan view cut through the trigger of a second embodiment of the surgical stapling instrument with the bayonet in the unlocked position.

FIG. 34 is an enlarged plan view showing the pivot pin structure in section taken along lines 34—34 of FIG. 35.

FIG. 35 is a side elevation of the instrument of FIG. 33.

FIG. 36 is a longitudinal section through the body of the instrument of FIG. 33.

FIG. 37 is a cross section through the pivot pin of FIG. 36.

FIG. 38 is a perspective view of the pusher hub.

FIG. 39 is a longitudinal section of the instrument of FIG. 36.

FIG. 40 is a cross section through the pivot pin of FIG. 39 with the trigger in elevation.

FIG. 41 is a side elevation of a second embodiment of the disposable cartridge showing the anvil-carrying and staple-carrying parts.

FIG. 42 is a top plan view of the staple-carrying part of FIG. 41 and the front of instrument of FIG. 33 with the bayonet sleeve in section.

FIG. 43 is an enlarged side elevation of the staple-carrying part and front of the instrument with the bayonet mounting structure in section.

FIG. 44 is a top plan view of the staple-carrying part locked onto the instrument of FIG. 35.

FIG. 45 is a side elevation of the structure illustrated in FIG. 44.

FIG. 46 is a sectional view of the bayonet assembly in the unlocked position as viewed along lines 46—46 of FIG. 43

FIG. 47 is the same view as FIG. 46 but with the bayonet assembly in the locked position.

FIG. 48 is a side elevation of the staple-carrying part of FIG. 41 with the main body part in section.

FIG. 49 is a sectional view taken along lines 49—49 of FIG. 48.

FIG. 50 is a bottom plan view of the staple-carrying part of FIG. 41 with a portion of the main body part in section.

FIG. 51 is a longitudinal section through the front end of the instrument illustrated in FIG. 33.

FIG. 52 is a bottom plan view of a portion of the rod and driver tube for the embodiment illustrated in FIG. 33.

FIG. 53 is a front end view of the structure illustrated in FIG. 52.

FIG. 55 is a sectional view taken along lines 55—55 of FIG. 54.

FIG. 56 is a partial section taken along lines 56—56 of FIG. 55.

FIG. 63 is a longitudinal section of the knife and support ring.

FIG. 64 is a partial plan view of the structure illustrated in FIG. 63.

FIG. 65 is a sectional view of the tip of the knife of FIG. 63.

FIG. 66 is a longitudinal section of the anvil-carrying assembly of FIG. 41.

FIG. 67 is an end plan view of the anvil-carrying assembly of FIG. 66.

FIG. 68 is a sectional view taken along lines 68—68 of FIG. 67 with the staples added.

FIG. 69 is a plan view of a portion of the anvil of FIG. 66.

FIG. 70 is a sectional view taken along lines 70—70 of FIG. 68.

FIG. 71 is a partial front elevation as viewed along lines 71—71 of FIG. 66.

FIG. 72 is a schematic view to show the detail of the top indexing key of the anvil of FIG. 66.

FIG. 73 is a schematic view to show the detail of the bottom indexing key of the anvil of FIG. 66.

DETAILED DESCRIPTION OF THE DRAWINGS

Figure 9:
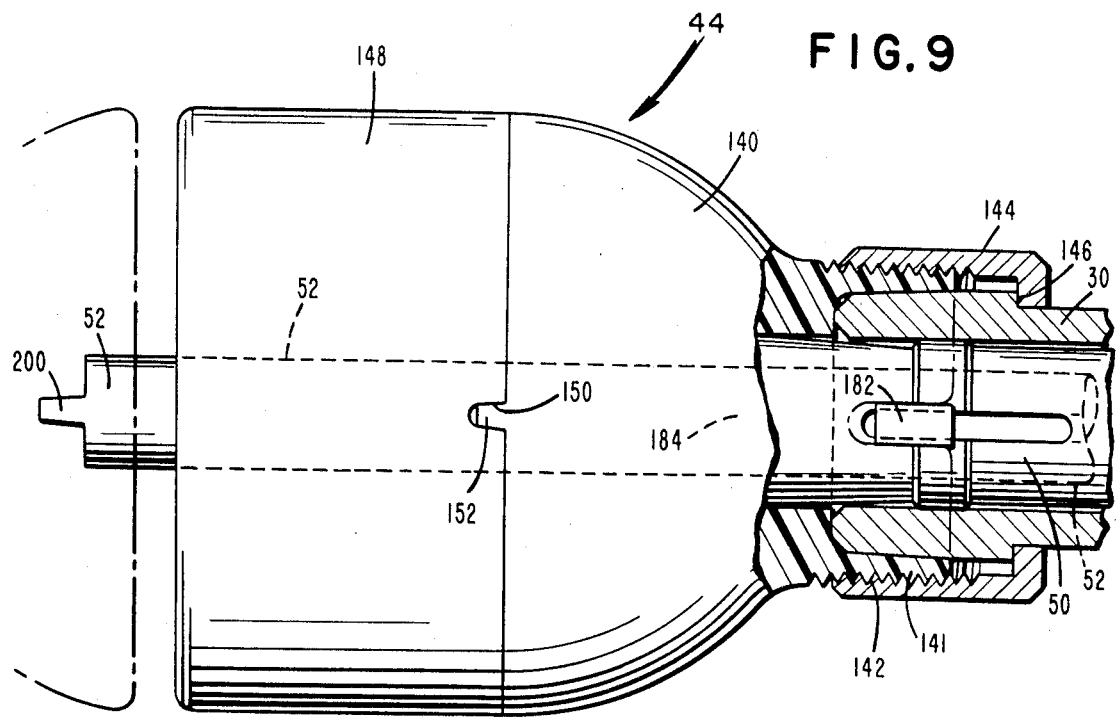
FIG. 9 is a view in top plan partly in section of the staple carrying part of the disposable cartridge showing the keying arrangement.

Referring now to the drawings in detail, a preferred embodiment of the instrument with disposable cartridge mounted thereon according to the teachings of the present invention is depicted in FIGS. 1 and 6. As shown, the instrument comprises a main body or housing defining a throughbore 11 and having an integrally formed rear handle part 12. Projecting from the body 10 is a pivotally mounted handle part 14, pivotably mounted to the body 10 by means of pivot pin 16. The handle part 12 is received in the palm of the hand of the operator and the handle part 14 is grasped by the fingers of the same hand. When the fingers are squeezed toward the palm, handle part 14 is pivoted about pin 16 and brought toward handle part 12. A conventional safety bar 18, terminating in a knob 20 bearing against the pivotable handle part 14 and which, in turn, is pivotally mounted on a pin 22 set into the body 10, serves as a safety to prevent the accidental actuation of handle part 14. Safety 18 is conventional in both function and structure.

Projecting from the forward end of the body or housing 10 is an outer tube 30 which extends forwardly and terminates at a substantial distance from housing 10. Received on the remote end of tube 30 is a disposable cartridge referred to generally by the reference numeral 40. Attachment of disposable cartridge 40 to the tube 30 is effected by means of a threaded coupling sleeve 42 in a manner which will be described hereinafter. This disposable cartridge 40 comprises a staple carrying member 44 and an anvil carrying member 46. Concentrically mounted within the tube 30, is a driver tube 50 and a rod 52. Driver tube 50 reciprocates within tube 30 and serves as a pusher for ejecting staples; the rod 52 reciprocates independent of driver tube 50 and serves to position the anvil carrying member 46 relative to the staple carrying member 44. The rod 52 extends entirely through the instrument with one end projecting out of the front of the instrument to receive and carry the anvil carrying member 46 and the other end projecting out of the back of the instrument through a wing nut 60. The rear end of the rod 52 is threaded as indicated to the right of FIG. 1 and is in threaded engagement with an internally threaded sleeve extension 110 of wing nut 60.

As illustrated in FIG. 3, the inside diameter of tube 50 is slightly enlarged intermediate its ends, for the purpose of relieving the contact between the rod 52 and driver tube 50 over a substantial area without any loss of function.

As shown in FIG. 5, an end cap 62 is applied to the rear of the instrument and effects a closure of throughbore 11. Cap 62 secures stepped bushing 304 against shoulder 306 in throughbore 11. The smallest bore through bushing 304 supports reduced part 106 of the rod 52 and terminates in bevelled shoulder 130. Holes 64 are provided in the cap 62 in order to accommodate a suitable spanner wrench to enable the attachment of the cap 62 into a suitably threaded terminal part of throughbore 11 at the rear end of the instrument. The cap 62 contains an external thread on its flange part that coacts or threadedly engages with the thread formed in the terminal part of throughbore 11.

Referring now to FIGS. 6, 7, and 8, the internal arrangement for the body or housing 10 will now be described in detail. As already noted, the cap 62 contains an external thread which threadedly engages with an internal thread suitably formed in the terminal part of the throughbore 11. This threaded engagement is identified generally by the reference numeral 66. Throughbore 11, at its end proximal to the disposable cartridge mounting, receives the outer tube 30 which extends into the throughbore 11 terminating at the entry to an enlarged region 70 of the bore 11. The body 10 and the tube 30 are rigidly interconnected in the bore 11 so that there is no relative motion between them. The driver tube 50 extends coaxially within the sleeve 30 and projects therefrom into the enlarged region 70 whereupon it is threadedly connected at its end by means of threads 74 with a short thicker sleeve 72. This sleeve 72, in turn, is connected by means of threads 76 with a terminating cap 78. This terminating cap 78 defines on its inner surface an inclined stop shoulder 81. The driver tube 50, together with the short sleeve 72 and the cap 78 being threaded together, all move as a unit. The short sleeve 72 being somewhat thicker than the driver tube 50 accommodates on either side a roller 80 which is mounted on a short stub shaft 88 pressed into a recess defined in the short sleeve 72. Rollers 80 are provided on diametrically opposed sides of the short sleeve 72 and serve as the means by which the driver tube 50 is reciprocated in the instrument. Also, the under side of the short sleeve 72 is provided with a suitable tapped hole 83 into which is threaded a projection 82. The stub or projection 82 extends downwardly, as portrayed in FIG. 8 of the drawings, and terminates in the plane of a slot 84 defined in the body 10. The purpose of the stub or projection 82 is to maintain a proper orientation for the driver tube 50 as it reciprocates back and forth; hence, stub or projection 82 in cooperation with slot 84 prevents driver tube 50 from rotating during reciprocation.

The arrangement for reciprocating the driver tube 50 is illustrated best in FIGS. 6 and 7. As already noted, the short sleeve 72 carries rollers 80 on diametrically opposed sides, the rollers 80 being mounted for free rotation by means of short stubs 88 which are pressed into the short sleeve 72 in the manner best illustrated in FIG. 7.

The handle part 14 is provided at its lower end with a bifuricated member 90, the legs of which are identified by the reference numeral 92. These legs 92 are fashioned as forks 94 which engage the rolers 80. The bifurcated member 90 is designed with an upstanding central projection 96 which fits into a slot 97 defined in the lower part of the handle part 14. Pins 98 projecting through holes formed in projection 96 hold the bifurcated member 90 to the handle part 14. Handle part 14 pivots about pin 16 as shown in FIG. 6, and forks 94 cooperating with rollers 80 cause driver tube 50 to reciprocate in tube 30. A spring 56 received around tube 50 in region 70 biases sleeve 72 against the reciprocation produced by handle part 14. The left end of spring 56 is held against the end of tube 30.

The rod 52 extends completely through the tube 30 and body 10 of the instrument. As will be evident from FIG. 8, the rod is provided with a bevelled shoulder 100 connecting the main portion of the rod 52 with a reduced portion 102 which, in turn, defines a bevelled shoulder 104 with a further reduced part 106 of the rod 52. The extreme right end of the rod is a further reduction in diameter, this portion being identified by the reference 108, and this reduced section 108 is threaded throughout its length.

The wing nut 60, which appears at the rear of the instrument, is provided with a sleeve extension 110. A reduced portion 112 interconnects sleeve 110 with the hub of nut 60, which reduction defines a groove into which a retaining ring 124 is received for the purpose of securing the wing nut 60 and its sleeve extension 110 onto the end cap 62. The sleeve extension 110, as well as nut 60, define a throughbore through which rod 52 passes. The bore within the sleeve extension 110 is threaded to threadedly engage with the threads defined on the reduced portion 108 of the rod 52. By the arrangement described, when the cap 62 is threaded into the body 10 with the wing nut 60 held thereon by means of the retaining ring 124, the wing nut 60 will not translate when rotated because of being secured to the end cap 62 in the manner described. Accordingly, sleeve extension 110, acting as a nut on threaded part of rod 108, will cause the rod 52 to reciprocate.

The bevelled shoulder 104 acts as a stop, working against a bevelled shoulder 130 defined in the bushing 304. The furthest position of the rod 52, that it may assume when driven to the right by means of sleeve extension 110, is illustrated in FIG. 8 with the bevelled shoulder 104 and the bevelled shoulder 130 in contact. This also represents the closest approach of the anvil carrying part 46 to the staple carrying part 44 of the disposable cartridge. This position of closest approach is illustrated in FIG. 1 and is selected to define a space between the two parts of the disposable cartridge that is equal to the minimum spacing required to accommodate tissue from whatever hollow body organs are to be stapled by the instrument of the present invention.

Figure 10:
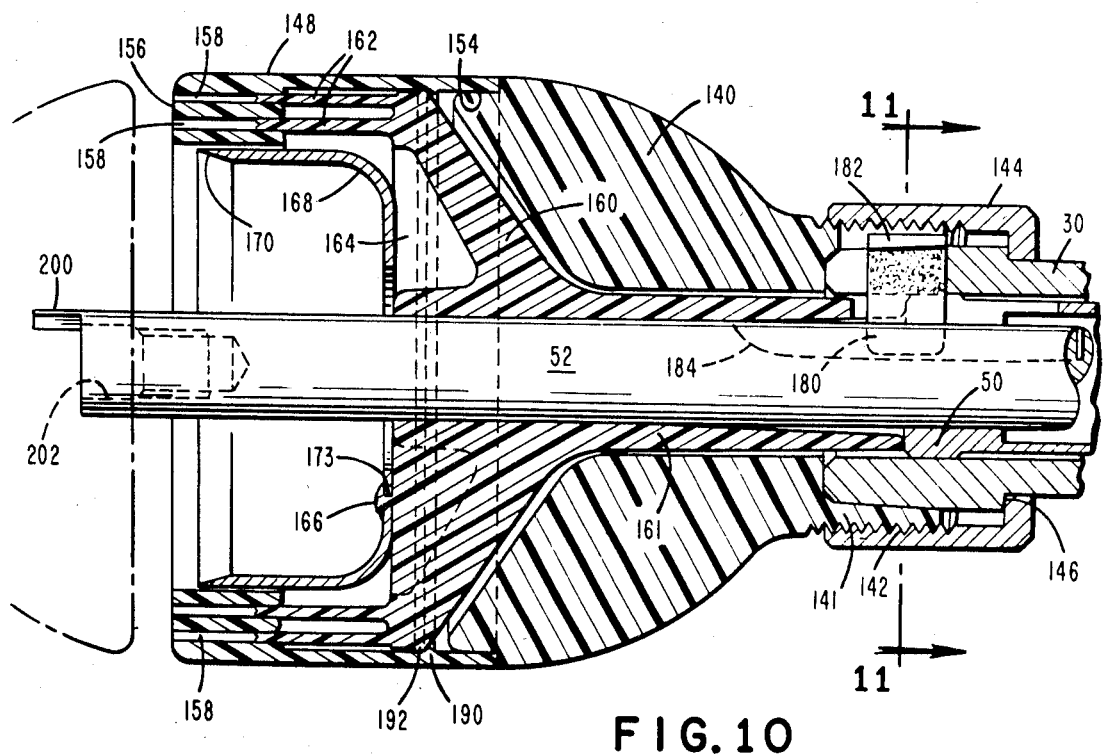
FIG. 10 is a view in section through the staple carrying part of the disposable cartridge.

Referring now to FIGS. 9, 10, and 11, the staple carrying part 44 of the disposable cartridge will now be described in detail. The part 44 is an assembly comprised of a main body portion 140 having an hemi-ovate shape terminating at its right end in a small diameter neck 141 having external threads 142. These threads 142 cooperate with an internally threaded coupling sleeve 144 which is retained on the end of the tube 30 by means of shoulder 146. A staple guide member 148 provided with a slot 150 coacting with a projection 152 defined on the main body part 140 for orientation is secured to the main body part 140 by an adhesive or the like, the area of securement being identified by the reference numeral 154. The guide member 148 forms a guide face 156 which defines a closed pattern of spaced staple receiving slots 158. The closed pattern preferably comprises two concentric circular series of spaced staple receiving slots or grooves 158. Received within the guide member 148 and the main body part 140 is a staple pusher member 160, which fits concentrically within the main body part 140, terminates in a long neck 161 and is adapted to be contacted by the end of driver tube 50. The forward end of the staple pusher 160 is defined with two concentric rings of peripherally spaced fingers 162, each one of which is received within a staple receiving slot 158. Hence, upon advancing the staple pusher 160 by driver tube 50, the fingers 162 will pass further into the staple receiving slots 158, ejecting staples contained therein axially outwardly. The staple pusher 160 is reinforced with a plurality of ribs 164, at least two of which are provided with suitable plastic projections or bosses 166. A knife 168, in the form of an open cup with the rim defining the knife edge 170, is mounted within the staple ejector 160 by means of holes 173 through which the bosses 166 project. In mounting, the bosses 166 are "hot staked" to fasten the knife 168 onto the staple ejector 160 so that advancement of the staple ejector 160 also advances knife 168.

A two-headed key 180 is press fitted into an opening or slot defined in the outer tube 30. The outer head 182 of the key is somewhat enlarged and coacts with a slot defined in the small neck of the main body part 140 to maintain this body part 140 and the associated guide member 148 in a predetermined indexed orientation with respect to the double-headed key 180. The driver tube 50 is provided with an elongated slot through which the key 180 passes in a loose fashion and the rod 52 is provided with a close fitting slot 184 into which the other end of the key 180 is received.

When initially assembled, the guide member 148 and the staple ejector 160, which define mutually opposed detents 190 and 192, respectively, are oriented such that detent 192 formed on the outer periphery of the staple ejector 160, is to the right of the detent 190 as shown in FIG. 13. The purpose of these mutually opposed detents is to prevent any outward motion of the staple ejector 160 and its associated knife 168, that is outward from the face 156, and thereby prevent any accidental discharge of staples or accidental projection of the knife, before assembly onto tube 30.

When the staple carrying part of the disposable cartridge is assembled onto the end of the outer tube 30 by means of the sleeve 142 and the mutually engaging threads of the sleeve and the small neck of the main body part 140, the main body part 140 will be drawn to a position such that the staple ejector 160 will engage the free end of the driver tube 50 and then be moved slightly outwardly relative to the main body part 140. This will cause the detents 190 and 192 to reverse themselves from the position shown in FIG. 13 to the position shown in FIG. 10. The staple carrying part 44 will then be ready for use.

The rod 52 is provided at its free end with a key 200 for the purpose of indexing the anvil carrying part 46 to the rod 52. The rod 52 is also provided at its free end with a tapped hole 202 for the purpose of detachably mounting the anvil carrying part 46.

The anvil carrying part 46 is illustrated in FIGS. 16–22, inclusive, and comprises a plastic body portion 210 of cup shape with a central hub 212 defining a bore 214. A stud 216 is received through the bore 214 and is characterized by knob 48 at one end and a screw thread 220 at its other end with a reduced section 222 defined between its ends. The threading 220 matches the internal threading of the bore at the end of rod 52. Clips 224, defined by the portion 210, project into the bore 214 and engage the shoulder defined by the reduced section 222 to hold stud 216 captive in bore 214, but allowing it to rotate freely. The body portion 210 in the vicinity of bore 214 has cutout 226 to accommodate the key 200 at the end of rod 52. Holes 49 provide venting for the anvil carrying part 46. Metal anvil 230, having a closed pattern in the form of two concentric circular arrays of spaced staple clinching grooves 232 and a central hole 233 is mounted onto body portion 210 by "hot staking". Body portion 210 defines a plurality of ribs 234 at least two of which are provided with projections or bosses 236. Anvil 230 defines matching holes 238 and, after mounting, bosses 236 are melted to form rivets 240 to lock anvil 230 on, see particularly FIG. 22. Anvil 230 is also provided with punched-out lips 242 to secure a cutting block 244 of annular configuration that cooperates with knife 168. Cutting block 244 is rubber, soft plastic, or the like. Anvil 230 defines a cutout or keyway 231 as an extension of hole 233 that coacts with key 200 to insure the proper orientation and indexing for grooves 232 of the anvil 230 relative to slots 158 of the staple carrying part 44. Anvil 230 has vent holes 47 which communicate with vent holes 49 in body 210.

In operation, wing nut 60 is rotated to advance rod 52 out from the end of tube 30. A staple carrying part 44 of a disposable cartridge 40 is fitted over rod 52 and tube 30 and attached to tube 30 by sleeve 42. The geometry of these parts is such that key 180 engages the neck of staple carrying part 44 before the threading engages to draw part 44 onto tube 30 to its seated position. During the last turns of sleeve 42, the end of driver tube 50 engages the staple pusher 160 to reverse the detents 190 and 92 from the position shown in FIG. 13 to the position shown in FIG. 10.

Next, the anvil carrying part 46 is assembled onto the end of projecting rod 52. To this end, the knob 48 is grasped and the pointed threaded end of stud 216 is introduced into the tapped hole in the end of rod 52. Key 200 is received at this time in keyway 231 of anvil 230 before the threading engages, whereafter knob 48 is rotated to seat threaded end 220 of stud 216 into the tapped hole at the end of rod 52 and draw the key 200 into the keyway 231. Keys 180 and 200 assure that slots 158 and grooves 232 are properly aligned. Wing nut 60 is then rotated to retract rod 52 and thus bring anvil part 46 close to staple carrying part 44.

Figure 23:
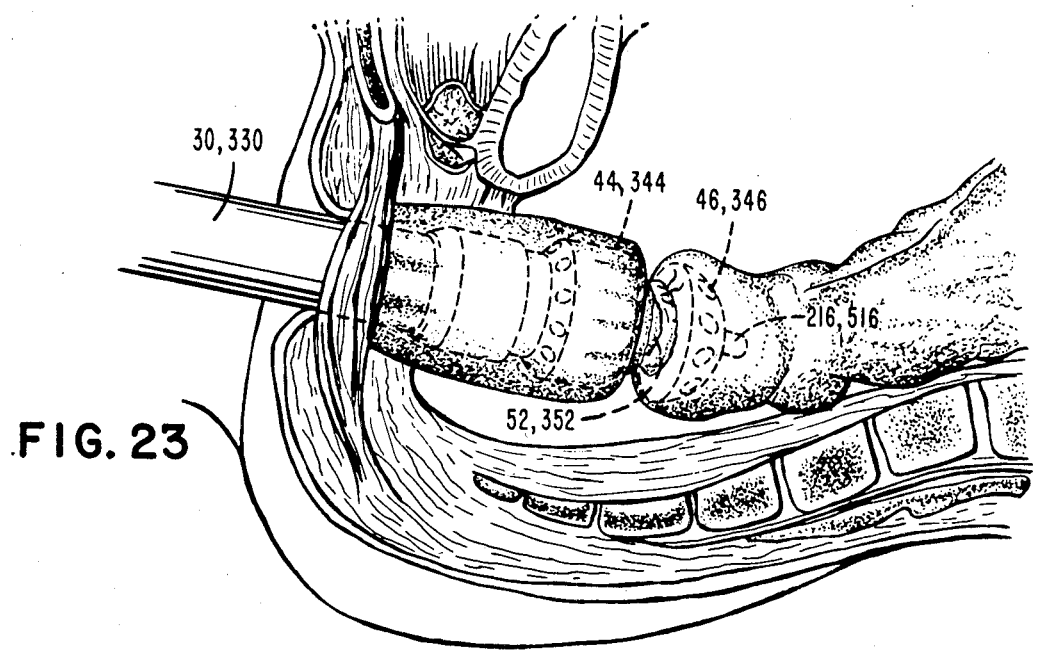
FIG. 23 is a graphic view of the instrument and disposable cartridge in use.
Figure 24:
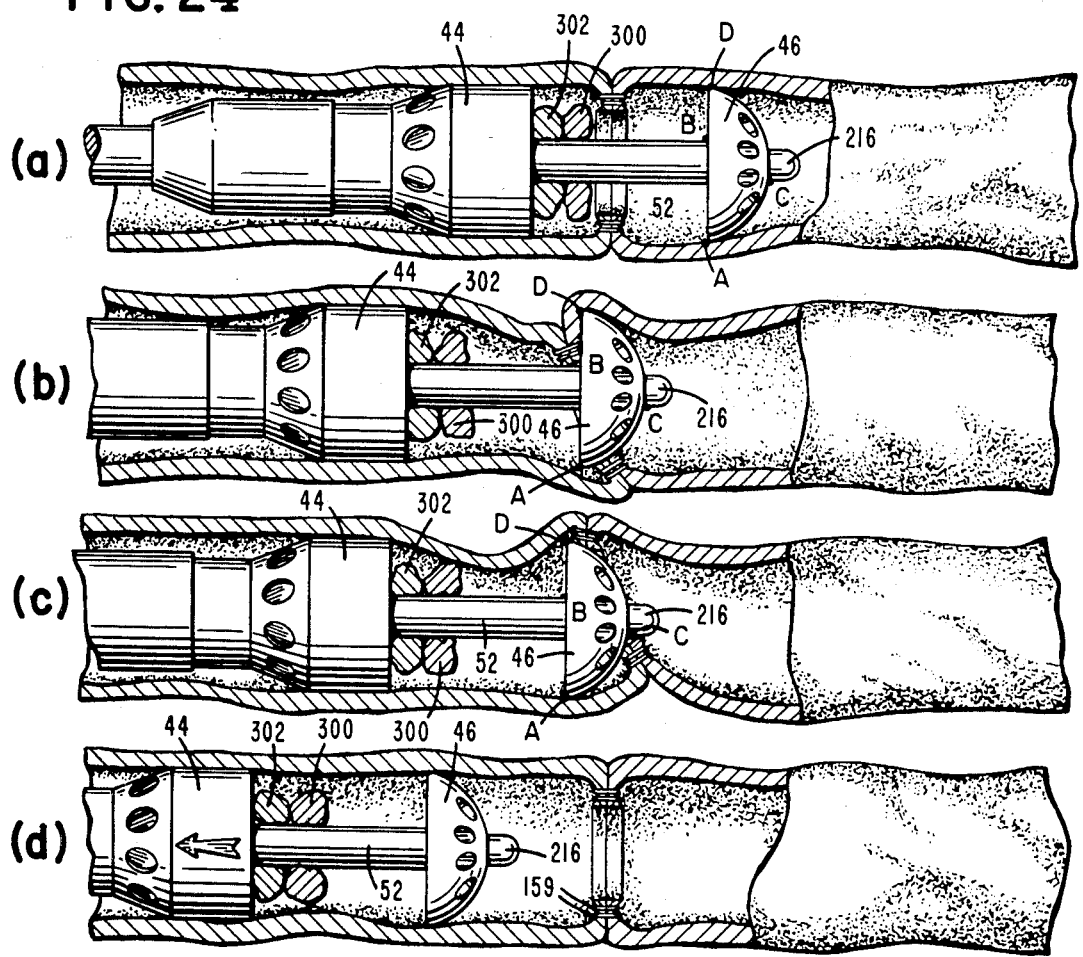
FIGS. 24(a) through 24(d) are schematic views illustrating the technique for removing the instrument and cartridge upon completion of a stapling operation.

In this condition, the instrument is inserted into the patient through the hollow organ that is to be stapled, see FIG. 23. At this time, the patient has been prepared such that the hollow organ to be stapled has been cut and there are two cut ends to be joined together by means of the instrument of the present invention. The instrument is inserted through the hollow organ until it projects from one of the cut ends. The wing nut 60 is rotated to extend the rod 52, thereby creating a substantial gap between the anvil carrying part 46 and the staple carrying part 44.

Now with reference to FIGS. 22 and 23 the cut end of the hollow organ, through which the instrument is protruding, is fashioned with a drawstring suture and drawn over the staple-carrying part 44 about the rod 52. The other cut end of the hollow organ is pulled over the anvil carrying part 46 and, by means of a drawstring suture, is tied closely about the rod 52. Thus, the two cut ends of the hollow organ will be interposed between the anvil part 46 and the staple carrying part 44. At this time, the wing nut 60 is rotated to cause retraction of the rod 52, whereupon the anvil-carrying part 46 will be brought into close proximity with the staple-carrying part 44. Wing nut 60 is turned until a predetermined space is filled by the tissue interposed between the staple carrying part 44 and the anvil carrying part 46.

At this time, the rod 52 will occupy a position within the body 10 of the instrument, as shown in solid lines in FIG. 8 with the stop 104 bearing against the stop 130. If there is a greater than minimum thickness of entrapped tissue, the stop 104 will be axially displaced off of the stop 130 to the left, as shown in phantom or some intermediate position. This closed position, to accommodate somewhat thicker tissues, is visually indicated by the emergence of a groove 51 in threaded end of rod 52 from wing nut 60, as shown in FIG. 1. Thus, the surgeon knows that if the groove 51 is at all visible, cartridge 44 is close enough to anvil assembly 46 to satisfactorily perform the stapling operation. When rod 52 seats at shoulder 104, the instrument is at its fully closed limit, and wing nut 60 cannot be further tightened.

With the apparatus in the condition described, that is, with the cut ends of the hollow organ to be stapled drawn around the two disposable parts of the cartridge and the instrument properly closed, the safety 18 is released by pivoting away from the handle part 14 toward the handle part 12 in the manner shown in phantom in FIG. 6 and the handle is grasped with the handle part 12 resting in the palm of the hand and the fingers curled about the handle part 14. When the fingers are drawn toward the palm of the hand in the manner of making a fist, the handle part 14 will be rotated clockwise about its pivot pin 16, as shown in FIG. 6, toward the handle part 12. This causes the forks 94 to advance the rollers 80 and the sleeve 72 axially to the left, as shown in FIG. 6, and as indicated by the arrow. This action will force the driver tube 50, which is threaded into the sleeve 72, to the left as viewed in FIG. 6, against the bias of spring 56. Advancement of driver tube 50 will, in turn, produce an advancement of the staple pusher 160, since the neck 161 of this part is in contact with the end of the driver tube 50. Advancement of the staple pusher 160 will cause the fingers 162 to move through the respective slots 158 ejecting the staples 159 contained therein. The action of the fingers 162 against the staples 159 is depicted in FIG. 15; the forward faces of the fingers 162 are all provided with a V-groove 163 in which the crossbar of the U-shaped staple 159 is received. This assures a better contact between the finger 162 and the staple 159 during ejection.

Referring to FIG. 21, the action that takes place during ejecting of the staple 159 is generally depicted; as the staples 159 are advanced or ejected out from the slots 158, they are contacted by grooves 232 of the anvil 230 and bent or formed into a conventional B-shape, as depicted in FIG. 21. Simultaneously with the advancement of the staple ejector 160, the knife 168, which is carried by the staple pusher 160, is axially advanced toward the anvil carrying part and the knife edge 170 of the knife 168 will intersect with the interposed tissue ends of the trapped hollow organs (shown in phantom in FIG. 22 at 300 and 302). The cutting edge 170 of the knife 168, which is circular in configuration, cuts through the tissues 300 and 302 and into the annular cutting block 244, which is held within the anvil 230 by means of the punched-out parts 242, as previously described. The advancing of driver tube 50 continues until stop 81 engages stop 100 on rod 52, the location of stop 100 being variable relative to cartridge 44 and body 10 in dependence upon tissue thickness. Stop 100, however, remains in constant positional relationship to anvil part 46, therefore driver tube 50 will advance to a predetermined distance relative to anvil part 46. Consequently, the pusher fingers 159 will always bend the staples into the same configuration. There is, as previously explained, a maximum limit to tissue thickness which a specific staple length can accommodate and which exists when wing nut 60 cannot be screwed down enough to expose groove 51. FIG. 22 depicts in phantom the two concentric circular arrays of staples 159 which join together the ends of the holow organ to be joined. The excess portion of the ends of the hollow organ to be joined are severed by the action of knife edge 170. During the closure of cartridge 44 against anvil part 46 to clamp the tissue prior to stapling, the interior space between the cartridge and anvil becomes essentially air and fluid tight. In this confined space are trapped the excess tissue of the hollow body organs which has been gathered around the center rod 52 by purse string sutures, as shown in FIG. 23, and the blood and other fluids associated with this tissue. Air is also trapped in this confined space. The tissue is extremely fluid and behaves like an incompressible fluid. Once sufficient contact has been made to create a seal between anvil part 46, tissue parts 300 and 302, and cartridge part 44, further tightening to clamp the tissue increases the pressure in the closed, confined space.

When the tissue is sufficiently clamped, the instrument is fired to eject and form the staples and to cut the tissue. The movement of parts within the confined space between the cartridge and anvil are best understood with reference to FIG. 10. When pusher tube 50 advances, the entire assembly of the pusher back 161, pusher fingers 162, and knife 168 advances toward the anvil 230 and significantly reduces the volume of the space in which the excess tissue is trapped. Because the tissue is mostly fluid and largely incompressible, this reduction in volume can create high pressures in the enclosed volume. To prevent this undesirable increase in pressure in the confined tissue, we have provided vent holes leading outward from the enclosed space. These are shown in FIGS. 17, 19 and 22. We have found it desirable to make these vent holes as large as feasible. In actual use of the instrument, it is common to find tissue in significant quantity extruded into and through these vent holes. It has been observed that without the vent holes, there is a definite tendency for the tissue to extrude outward between the clamped faces of the cartridge and anvil so as to literally curl outward the cutting edge 170 of circular knife 168. The severed ends 300 and 302 of the hollow organ are retained around center rod 52 between the anvil carrying part 46 and the staple carrying part 44.

The next step in the procedure would be to rotate wing nut 60 to increase the spacing between the anvil carrying part and the staple carrying part to allow the stapled part of the hollow organ to be withdrawn from between these instrument parts and passed over the anvil carrying part 46, so that the instrument may be withdrawn. To this end, the anvil carrying part 46 is provided with an external configuration typically of spherical dish-shape to facilitate the removal of the stapled organ from between the two parts 46 and 44 and passing of the stapled part of the organ over part 46. This removal is best accomplished when the perimeter of the profile, in section through the axis as shown in FIG. 16, of the anvil carrying part 46 is equal to or less than the circumference of the inner ring of staples represented by the inner circular array of spaced staple clinching grooves 232 in FIG. 19.

The removal of the circular stapled seam line over the anvil part 46 presents a problem because the inner circle line of staples cannot be stretched to any extent without damaging the stapled tissue. This is true, even though the tissue itself is readily stretched without damage due to its elasticity and resilience, because the staples are not elastic. Accordingly, the stapled circular seam must be manipulated over the anvil part 46 without being stretched. The small margin of free tissue within the inner staple circle is resilient and does not limit this manipulation as does the staple line itself.

The technique for removal of the anvil part 46 from the stapled anastomosis is shown schematically in FIGS. 24(a) through 24(d), and graphically in FIGS. 25 through 32. After the anvil 46 is moved sufficiently away from the cartridge 44 (FIG. 24(a)), the staple anastomosis line is moved to maximum eccentricity with rod 52. Then the staple line is slipped over the edge of anvil 46 at A (FIG. 24(b)) and moved progressively in this manner until the staple line encircles the anvil part across the section C-B in FIG. 25. Next the opposite point of the staple line at B is moved progressively outward toward D (FIG. 24(c)). Next the staple line is slipped over the perimeter of anvil part 46 at D whereupon the anvil is free to be withdrawn from the anastomosis (FIG. 24(d)).

Figure 25:
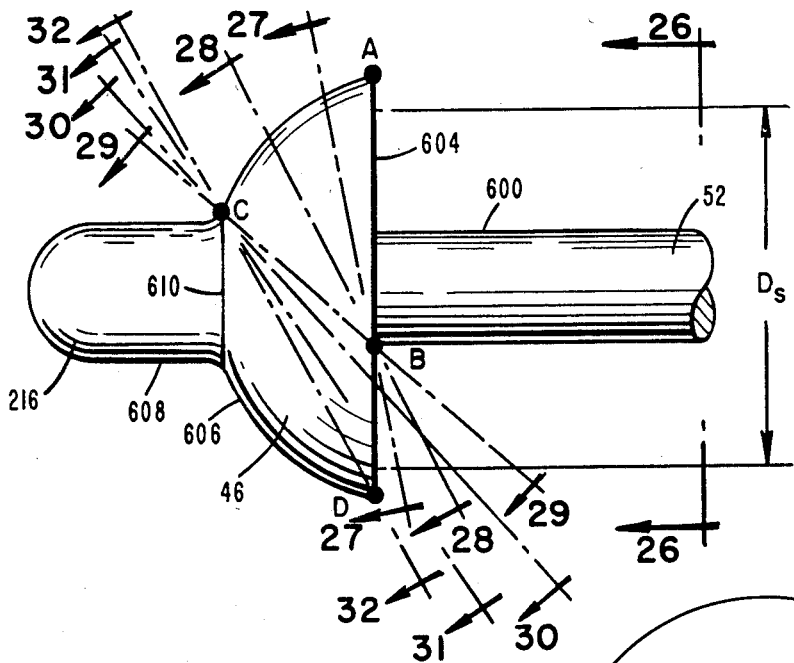
FIG. 25 is a graphic view to be used in conjunction with FIGS. 24(a) through 24(d).

The geometry of anvil part 46 must be such that all perimeters of cross sections of the anvil part encountered by the staple line in moving over the anvil part from A-B to C-B be equal to or less than the circumference of the inner circular staple line, the diameter of which is noted as $D_s$ in FIG. 25. Additionally, all perimeters of the anvil part encountered by the staple line in moving over the anvil part from C-B to C-D must be equal to or less than the circumference of the inner circular staple line. As a practical matter, the limiting perimeter has been found to be that represented by C-B.

Figure 26:
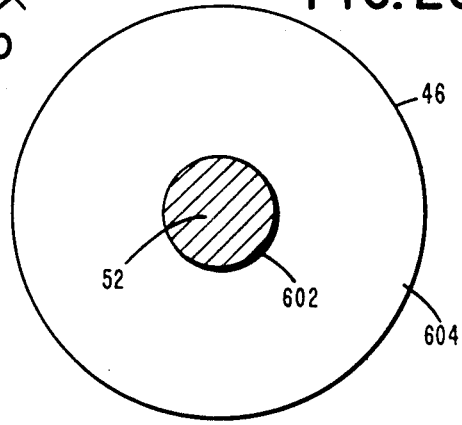
FIG. 26 is a graphic rear view of the anvil carrying structure as viewed along lines 26—26 of FIG. 25.
Figure 27:
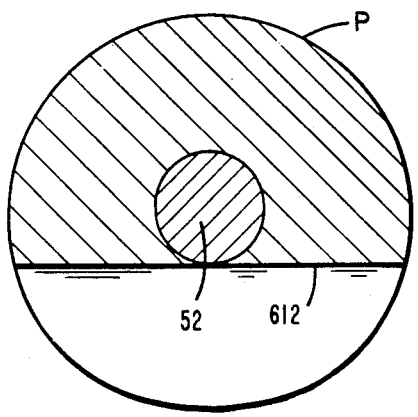
FIGS. 27 through 32 are graphic sectional views of the anvil carrying structure when cut by the various cutting planes set out in FIG. 25.
Figure 28:
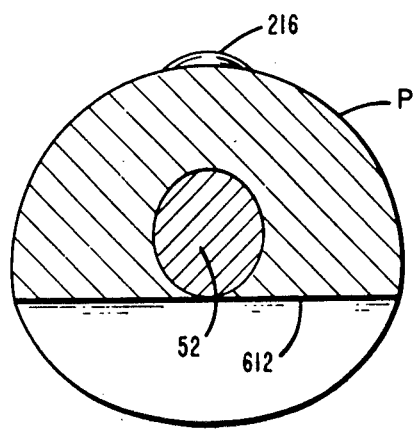
Figure 29:
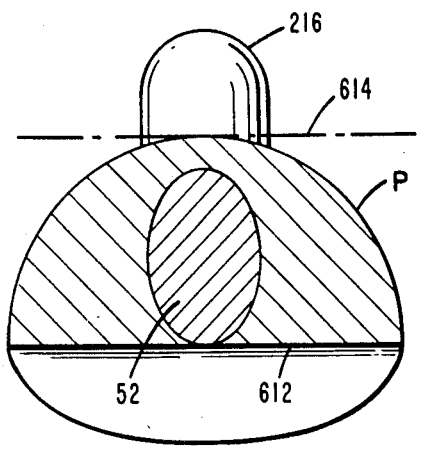
Figure 30:
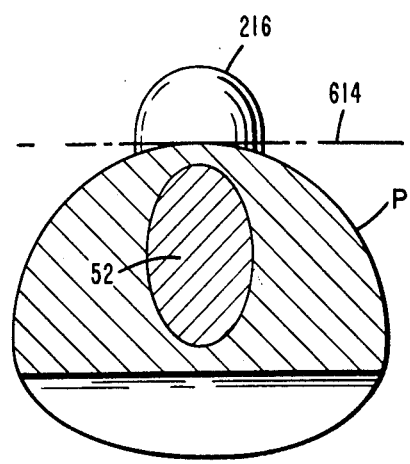
Figure 31:
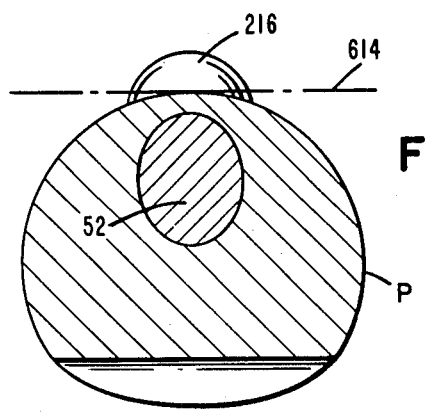
Figure 32:
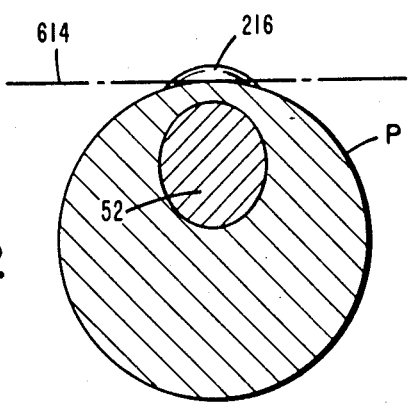
Figure 54:
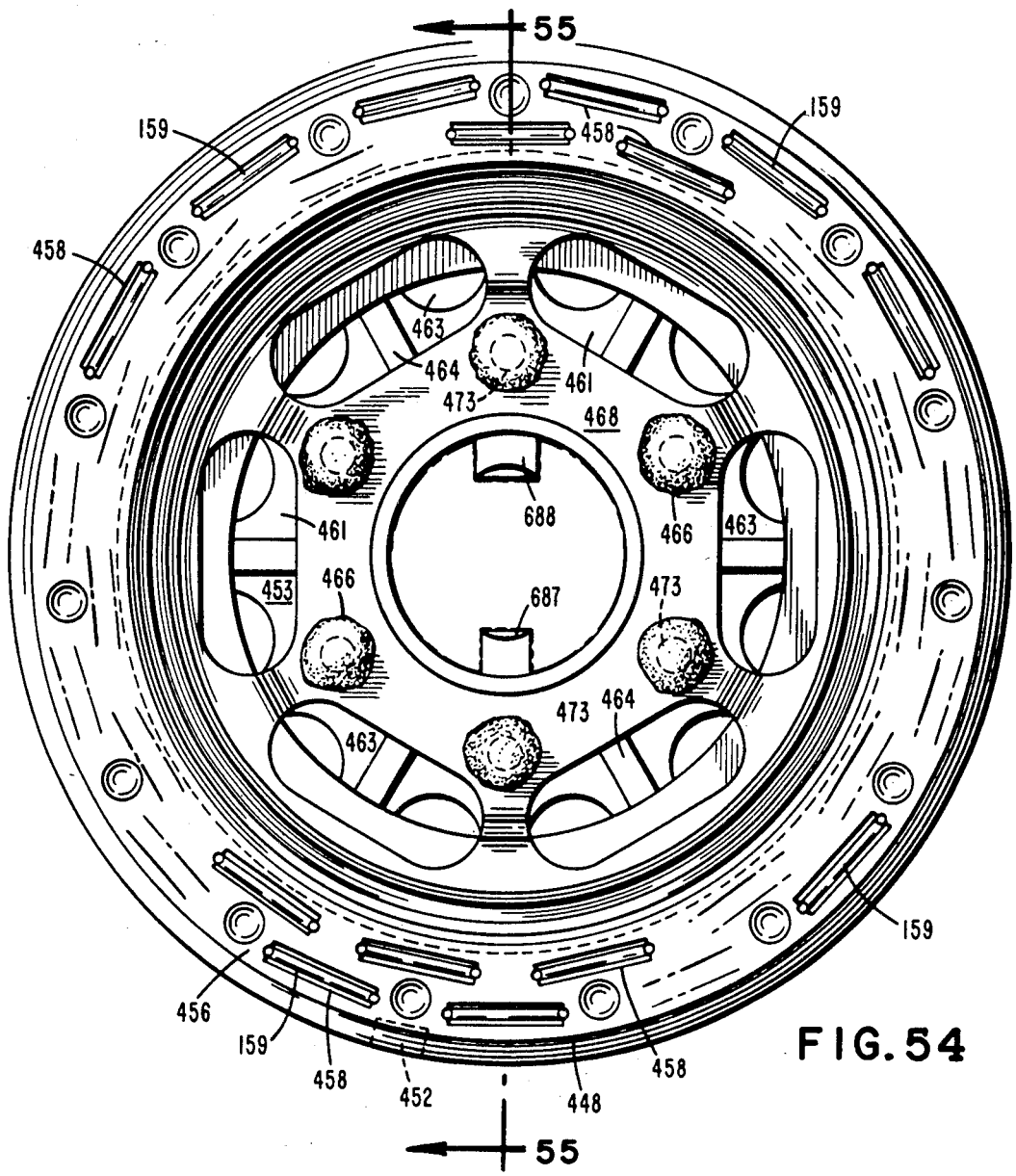
FIG. 54 is a front elevation of the fully assembled staple-carrying part of FIG. 41.
Figure 60:
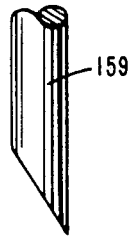
FIGS. 60 through 62 show the details of the staples.
Figure 61:
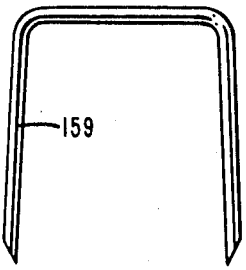
Figure 62:
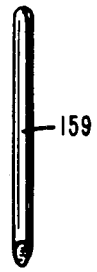
Figure 58:
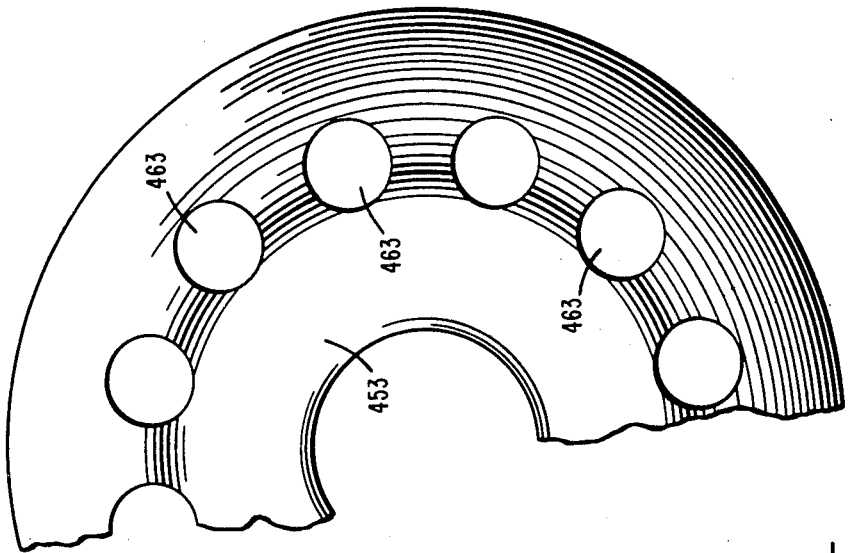
FIG. 58 is a rear elevation of the pusher back illustrated in FIG. 57.
Figure 57:
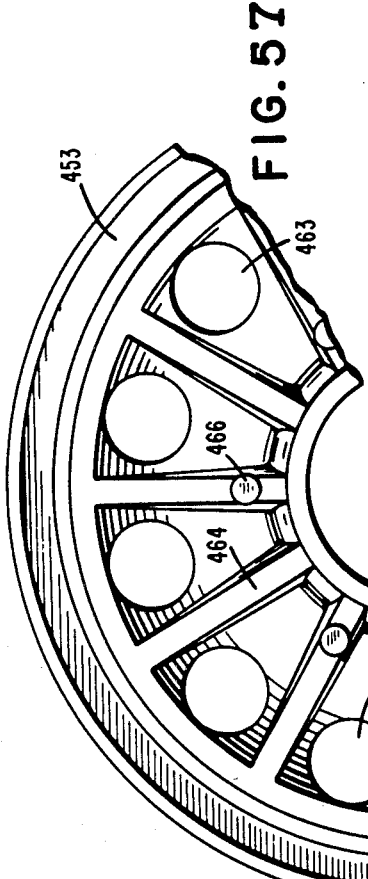
FIG. 57 is a front elevation as viewed along lines 57—57 of FIG. 55.
Figure 59:
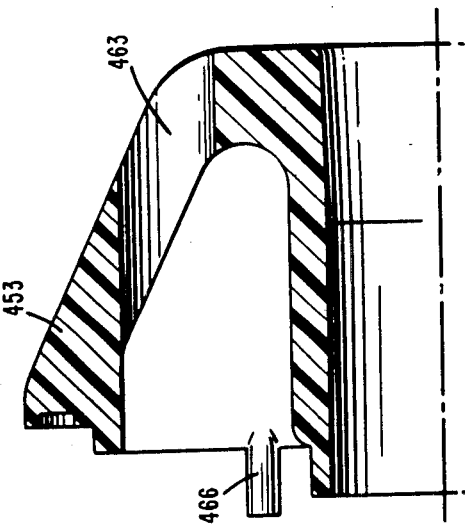
FIG. 59 is a partial section through one of the vent holes of the pusher back of FIG. 57.

In other words the anvil-carrying part 46 includes two concentric circular arrays of spaced staple clinching grooves 232 in a closed pattern. The rod 52, upon which the anvil carrying part 46 is mounted, intersects a plane 604 defined by the staple clinching grooves, and is typically concentric within the circular arrays of spaced clinching grooves. The intersection of the exterior surface 600 of the rod 52 with the plane 604 defines a closed geometric FIG. 602. FIG. 26, which graphically illustrates a view taken from a plane parallel to the plane 604 defined by the circular arrays of spaced clinching grooves, shows the closed geometric FIG. 602.

The anvil carrying part 46 has a geometric shape related to the circumference of the inner one of the pair of concentric circular arrays of staple clinching grooves. In order to explain the relationship, provision is made in FIGS. 25 and 27–29 for a plurality of cutting planes, other than the cutting plane parallel to the surface of the array of spaced staple clinching grooves, which pass through the anvil carrying part 46 and include a line 612 tangent to the exterior of said closed geometric figure, which line of tangency lies within the plane of the staple clinching grooves. When the cutting plane is rotated about the line of tangency 612, the plane defines sections, illustrated in FIGS. 27 through 29, of the anvil-carrying part 46 all of which have a perimeter P equal to or less than the circumference of the inner one of the pair of concentric circular arrays of staple clinching grooves.

Again, with reference to FIG. 25, knob 216 is used to secure the anvil-carrying part 46 to the rod 52. The knob 216 intersects the exterior surface 606 of the anvil-carrying part 46. The intersection of the exterior surface 608 of the knob 216 with the exterior surface 606 of the anvil-carrying part 46 defines a closed geometric FIG. 610.

The anvil-carrying part 46 has a geometric shape related to the circumference of the inner one of the pair of concentric circular arrays of staple clinching grooves. In order to explain the relationship, provision is made in FIGS. 25 and 29–32 for a plurality of cutting planes which pass through the anvil-carrying part 46 and include a line 614 tangent to the exterior of the closed geometric FIG. 610. When the cutting plane is rotated about the line of tangency 614, the plane defines sections, illustrated in FIGS. 30 through 32, of the anvil-carrying part 46 all of which have a perimeter P equal to or less than the circumference of the inner one of the pair of concentric circular arrays of staple clinching grooves.

Referring now to FIGS. 33 through 73, another preferred embodiment of the instrument with disposable cartridge is depicted. As shown in FIGS. 33 through 40, the instrument comprises a main body or housing 310 defining a throughbore 311 and having an integrally formed rear handle part 312. Projecting from the body 310 is a handle part 314, pivotably mounted to the body 310 by means of pivot pin assembly 316. The handle part 312 is received in the palm of the hand of the operator and the handle part 314 is grasped by the fingers of the same hand. When the fingers are squeezed toward the palm, handle part 314 is pivoted about pin 316 and brought toward handle part 312. A safety bar 318, terminating in a knob 320 is pivotally mounted on a pin 322 set into the body 310, and serves as a safety to prevent the accidental actuation of handle part 314 as shown by the arrow in FIG. 35. As best seen in FIG. 36, a set screw 323 is received in a threaded bore 325, contained in handle part 314. The set screw is adjusted and secured by a suitable adhesive, so that the safety bar 318 can move into a locked position without binding on its flat face 321.

Projecting from the forward end of the body or housing 310 is an outer tube 330 which extends forwardly and terminates at a substantial distance from housing 310. Received on the remote end of tube 330, as best seen in FIG. 41, is a disposable cartridge referred to generally by the reference numeral 340. Attachment of staple carrying member 344 to the tube 330 is effected by means of a bayonet-connecting sleeve 342 in a manner which will be described hereinafter. This disposable cartridge 340 comprises a staple-carrying member 344 and an anvil-carrying member 346.

With reference to FIGS. 35–40, concentrically mounted within the tube 330, is a driver tube 350 and a rod 352. Driver tube 350 reciprocates within tube 330 and serves as a pusher for ejecting staples; the rod 352 reciprocates independent of driver tube 350 and serves to position the anvil-carrying member 346 relative to the staple-carrying member 344. The rod 352 extends entirely through the instrument with one end projecting out of the front of the instrument to receive and carry the anvil-carrying member 346 and the other end projecting out of the back of the instrument for receiving a wing nut 360. The rear end of the rod 352 is threaded and is in threaded engagement with an internally threaded sleeve extension 410 of wing nut 360.

As shown in FIGS. 36 and 39, an end cap 362 is applied to the rear of the instrument and effects a closure of throughbore 311. Cap 362 secures stepped bushing 704 against shoulder 706 in throughbore 311. The smallest bore through bushing 704 supports reduced part 408 of the rod 352. The cap 362 contains an external thread that coacts, or threadedly engages, with the thread formed in the terminal part of throughbore 311.

Referring now to FIGS. 36 through 40, the internal arrangement for the body or housing 310 will now be described in detail. As already noted, the cap 362 contains an external thread which threadedly engages with an internal thread suitably formed in the terminal part of the throughbore 311. This threaded engagement is identified generaly by the reference numeral 366. Throughbore 311, at its end proximal to the disposable cartridge mounting, receives the outer tube 330 which extends into the throughbore 311 terminating at the entry to an enlarged region 370 of the bore 311. The body 310 and the tube 330 are rigidly interconnected in the bore 311 by holding pin 361, so that there is no relative motion between them. The driver tube 350 extends coaxially within the sleeve 330 and projects therefrom into the enlarged region 370 whereupon it is fixedly mounted at its end within a pusher hub 372. This hub 372, in turn, is connected by means of threads 376 with a pusher-stop cap 378. The driver tube 350, together with the pusher hub 372 and the cap 378, all move as a unit.

With reference to FIGS. 36 and 38, the pusher hub 372 is of generally cylindrical shape with a stepped throughbore 371. The larger portion 373 of the bore 371 receives and mounts the reduced end of the driver tube 350. The smaller portion 375 of the bore 371 is of sufficient diameter to allow the rod 352 to freely slide therethrough. Cutout portions 380 are provided on diametrically opposed sides of the hub 372. These cutouts cooperate with the trigger 314 in a manner described hereinafter to serve as the means by which the driver tube 350 is reciprocated within the outer tube 330 of the instrument.

The arrangement for reciprocating the driver tube 350 is illustrated best in FIGS. 36 through 40. As already noted, the pusher hub 372 carries the cutouts 380 on diametrically opposed sides. The handle part 314 is provided at its lower end with a yoke 390, the legs of which are identified by the reference numeral 392. These legs 392 are received in the cutouts 380, each of which contains a front wall 391 and a back wall 393.

Pivoting of trigger 314 about pin 316 results in a longitudinally-directed force being exerted on the front walls 391 of the hub 372 by yoke portion 390 of the trigger 314. This results in the forward movement of driver tube 350 within outer tube 330. A spring 356 received around tube 350 in region 370 biases hub 372 against the foward movement produced by handle part 314. The left end of spring 356, as viewed in FIG. 39, is held against the end of tube 330

The rod 352 extends completely through the tube 330 and body 310 of the instrument. The rod is provided with a reduced portion 400 bounded at its rearend by bevelled shoulder 402. Provided near the front of the reduced portion 400 is an indicator groove 403. A groove 405 connects the main portion of the rod with a reduced portion 406, which, in turn, is connected to a threaded reduced portion 408 via a groove 707.

The wing nut 360, which appears at the rear of the instrument, is provided with a sleeve extension 410. The nut 360 is secured to the sleeve extension by a pair of pins 412. A retaining ring 424 is received into a groove 413 for the purpose of securing the wing nut 360 and its sleeve extension 410 onto the end cap 362. The sleeve extension 410, as well as nut 360, defines a throughbore through which rod 352 passes. The front portion of the bore within the sleeve extension 410 is threaded to threadedly engage with the threads defined on the reduced portion 408 of the rod 352. By the arrangement described, when the cap 362 is threaded into the body 310 with the wing nut 360 held thereon by means of the retaining ring 424, the wing nut 360 will not translate when rotated because of being secured to the end cap 362 in the manner described. Accordingly, sleeve extension 410, acting as a nut on threaded part of rod 408, will cause the rod 352 to reciprocate.

The shoulder 401 of reduced portion 406 acts as a stop working against a shoulder 430 defined in the bushing 704. The furthest position of the rod 352, that it may assume when driven to the right by means of sleeve extension 410, is illustrated in FIG. 36 with the shoulder 401 and the shoulder 430 in contact. This also represents the closest approach of the anvil carrying part 346 to the staple carrying part 344 of the disposable cartridge. This position of closest approach is illustrated in FIG. 39 and is selected to define a space between the two parts of the disposable cartridge that is equal to the minimum spacing required to accommodate tissue from whatever hollow body organs are to be stapled by the instrument of the present invention.

With reference to FIGS. 41 through 59, the staple-carrying part 344 is an assembly comprised of a hollow main body portion or shell 440 having a cylindrical portion and a frusto-conical portion which terminates in a small diameter neck 441. As best seen in FIG. 50, a staple guide member 448 provided with a projection 452 coacting with a slot 450 defined on the main body part 440 for rotational orientation is secured to the main body part 440. The guide member 448 forms a guide face 456 which defines two concentric circular series of spaced staple-receiving slots 458, see FIG. 54. Holes 451 provide venting for the staple-carrying part 344. Received within the main body part 440, as shown in FIGS. 50 and 55 is a staple pusher assembly 460, which fits concentrically within the main body part 440. The rear portion of the staple ejection assembly 460 is defined by a pusher back 453 having a generally frusto-conical shape and containing vent holes 463. The forward portion of the staple pusher 460 is defined by a member 455 which contains two concentric rings of peripherally spaced fingers 462, each one of which is received within a stape receiving sot 458. The member 455 is secured to the pusher 453 by a suitable adhesive at a point 457. The rear end 461 of the staple pusher 453 is adapted to be contacted by the end of driver tube 350. Hence, upon advancing the staple pusher assembly 460 by driver tube 350, the fingers 462 will pass furlher into the staple receiving slots 458, pushing staples contained therein axially outwardly. The staple pusher 460 is reinforced with a plurality of ribs 464 (FIG. 57), at least two of which are provided with suitable plastic projections or bosses 466. With reference to FIGS. 54 and 63 through 65, a knife 468 in the form of an open cup with the rim defining the knife edge 470 is mounted within the staple ejector assembly 460 by means of holes 473 through which the bosses 466 project. In mounting, the bosses 466 are "hot staked" to fasten the knife 468 onto a support ring 467 of the the staple ejector assembly 460 so that advancement of the staple ejector 460 also advances knife 468. The knife 468 has vent holes 461 which communicate with the vent hoes 463 in the pusher 453.

As best seen in FIGS. 48 through 51, a shell support liner 576 of generally cylindrical shape is press fitted into the end of the small diameter neck 441. The liner 576 contains a pair of bayonet projections 578 and a guide projection 580, all of which mate with slots 581-583, respectively, to ensure proper indexing of the liner 576 when it is fitted into the neck 441. Defined within the liner 576 is a tube bore 584 of predetermined depth and which is of sufficient diameter to be slidably mounted on the flanged end of tube 330. Contained within the liner 576 is a keyway 586, which mates with key 588 to ensure proper orientation of the staple-carrying part 344 with respect to the tube 330. An additional bore 710 of smaller diameter than bore 584 is provided for in liner 576; bore 710 is of sufficient diameter to allow tube 350 to freely slide therethrough. Bore 710, as viewed in FIG. 49, contains a pair of inwardly extending support members 686, which pass through slots 353 (FIGS. 42 and 52) in tube 350. The inner ends of members 686 define both a diameter 689 which fits closely with rod 352, and two keys 687 and 688 which mate respectively with slots 458 and 459 in rod 352. The keys, 687 and 688, and the slots 458 and 459, are of two different widths so that there is only one position in a 360° rotation in which the parts can be assembled.

It is paramount that the anvil 530 be in precise alignment with cartridge part 344 in all respects. In the above construction, the cartridge is aligned and keyed to center rod 352. As will be explained below, the anvil 530 is also aligned and keyed to the same slots 458 and 459 in rod 352. Since rod 352 is the single member connecting cartridge 344 and anvil 530 during the stapling procedure, an alignment path through the least number of parts (in order to obtain a minimum build up of error through accummulated tolerances, clearances, etc.) has been provided.

When the staple-carrying part 344 of the disposable cartridge 340 is assembled onto the end of the outer tube 330 by means of bayonet-connecting sleeve 342 and the bayonet pins 578 of the main body part 440 as shown in FIGS. 42 through 47, the main body part 440 will be drawn to a position such that the staple ejector 460 will engage the free end of the driver tube 350 and then be moved slightly outwardly relative to the main body part 440. The staple-carrying part 344 will then be ready for use.

The anvil-carrying part 346 is illustrated in FIGS. 41 and 66 through 73, inclusive, and comprises a body portion 510 of cup shape with a central hub 512 defining a knob-receiving bore 514 and "D" shaped bore 566. A knob 516 is received within the bore 514. A skirt 568, defined by the hub 512, projects over the bore 514 and engages the shoulder defined by the reduced section 522 to hold knob 516 captive in bore 514, but allowing it to rotate freely. A longitudinal bore 570 is provided in the knob 516. The bore 570, at its forward portion, contains internal threading 520, which matches the threading at the end of rod 352. The bore 566 contains an inner flat portion 565 to accommodate the flat 500 at the end of rod 352. Holes 349 provide venting for the anvil carrying part 346. Metal anvil 530, having two concentric circular arrays of spaced staple clinching grooves 532 and a central hole 533, is mounted onto body portion 510 by press-fitting. The central hole 533 has the same cross-sectional configuration as the "D" shaped bore 566. Outwardly projecting keys 541, 542 mate with slots 458, 459, respectively, on rod 352 to further ensure proper orientation of the anvil carrying part 346 with the rod 352. The keys 541, 542 are of different widths so that there is only one position in a 360° rotation which will permit assembly. Thus the anvil 530 is keyed to rod 352 and slots 458, 459 therein in the same manner as is staple-carrying part 344. To emphasize, this construction provides a minimum build up in tolerances and clearances in the assembly path connecting the anvil and the staple-carrying part when the staples are formed.

Anvil 530 supports a cutting block 544 of annular configuration, that cooperates with knife 468. Cutting block 544 is rubber, soft plastic, or the like. Anvil 530 has vent holes 347 which communicate with vent holes 349 in body 510.

In operation, wing nut 360 is rotated to advance rod 352 out from the end of tube 330. A staple-carrying part 344 of a disposable cartridge 340 is fitted over rod 352 and tube 330 and attached to tube 330 by a bayonet mount which includes bayonet pins 578 in the cartridge 340 and bayonet-receiving slots 357 in the sleeve 342. As shown in FIGS. 42 through 47, bayonet-connecting sleeve 342 is slidably mounted on tube 330. A cutout portion 341 of sleeve 342 and a pin 343 in tube 330 ensure the proper orientation of the sleeve 342 when it is slidably mounted on tube 330. A retaining ring 345, mounted in a groove on the tube 330 and a wall 747 in the sleeve 342, limit the return movement of the sleeve 342. A wall 349, defined by the flanged portion 351 of the tube 330 and a wall 353, defined by sleeve 342 in cooperation with spring 756 bias sleeve 342 rearwardly to hold staple carrying member 344 firmly against end of tube 351.

Next, the anvil-carrying part 346 is assembled onto the end of projecting rod 352. To this end, the knob 516 is grasped and the threaded end of rod 352 is introduced into the hole 570 having threaded portion 520. Flat 500 of rod 352 is received at this time in D hole 565 of anvil 510 before the threading engages, whereafter, knob 516 is rotated to seat threaded end of rod 352 into the threaded portion 520 of hole 570 and draw the flat 500 into the "D" hole 565. Keys 541, 542 assure that staple-carrying slots 458 and staple-clinching grooves 532 are optimally aligned. As previously explained, keys 541, 542 are differently sized so that anvil 530 cannot be positioned 180° out of rotational alignment. Wing nut 360 is then rotated to retract rod 352 and thus bring anvil-carrying part 346 close to staple-carrying part 344.

In this condition, the instrument is inserted into the patient through the hollow organ that is to be stapled. At this time the patient has been prepared such that the hollow organ to be stapled has been cut and there are two cut ends to be joined together by means of the instrument of the present invention. The instrument is inserted through the hollow organ until it projects from one of the cut ends. The wing nut 360 is rotated to extend the rod 352, thereby creating a substantial gap between the anvil carrying part 346 and the staple carrying part 344.

Now, the cut end of the hollow organ, through which the instrument is protruding, is fashioned with a drawstring suture and drawn over the staple-carrying part 344 about the rod 352. The other cut end of the hollow organ is pulled over the anvil-carrying part 346 and, by means of a drawstring suture, is tied closely about the rod 352. Thus, the two cut ends of the hollow organ will be interposed between the anvil part 346 and the staple-carrying part 344. At this time, the wing nut 360 is rotated to cause retraction of the rod 352, whereupon the anvil carrying part 346 will be brought into close proximity with the staple carrying part 344. Wing nut 360 is turned until marker ring 403 on rod 352 lies within the width of marker 404 on body 310. These marks have been preestablished to ensure that the tissue is clamped to a thickness which can be satisfactorily joined by the staples being used. The maximum clamping of tissue interposed between the staple-carrying part 344 and the anvil-carrying part 346 exists when shoulder 401 of rod 352 abuts shoulder 430 of bushing 704.

At this time, the rod 352 will occupy a position within the body 310 of the instrument, either as shown in solid lines in FIG. 39 with the stop 401 bearing against the stop 430, or due to a greater than minimum thickness of entrapped tissue, the stop 401 will be axially displaced off of the stop 430 to the left, as shown in phantom.

With the apparatus in the condition described, that is, with the cut ends of the hollow organ to be stapled drawn around the two disposable parts of the cartridge, the safety 318 is released by pivoting away from the handle part 314 toward the handle part 312 in the manner shown in FIG. 35, and the handle is grasped with the handle part 312 resting in the palm of the hand and the fingers curled about the handle part 314. When the fingers are drawn toward the palm of the hand in the manner of making a fist, the handle part 314 will be rotated about its pivot pin 316 clockwise, as shown in FIG. 39, toward the handle part 312. This causes the yoke 390 to advance the pusher hub 372 axially to the left, as shown in FIG. 39, and as indicated by the arrow. This action will force the driver tube 350, which is mounted into the hub 372 to the left as viewed in FIG. 39, against the bias of spring 356. Advancement of driver tube 350 will, in turn, produce an advancement of the staple pusher 460, since the rear end 461 of this part is in contact with the end of the driver tube 350. Advancement of the staple pusher 460 will cause the fingers 462 to move through the respective slots 458 ejecting the staples 159 contained therein. The action of the fingers 462 against the staples 159 is depicted in FIGS. 48 and 68; the forward faces of the fingers 462 are all provided with a V-groove 463 in which the crossbar of the U-shaped staple 159 is received. This assures a better contact between the finger 462 and the staple 159 during ejection.

Referring to FIGS. 48, 50, and 68 through 71, the action that takes place during ejecting of the staple 159 is generally depicted; as the staples 159 are advanced or ejected out from the slots 458, they are contacted by grooves 532 of the anvil 530 and bent into a conventional B-shape, as depicted in FIG. 70. Simultaneously with the advancement of the staple pusher 460, the knife 468, which is carried by the staple pusher 460, is axially advanced toward the anvil-carrying part and the knife edge 470 of the knife 468 will intersect with the interposed tissue ends of the trapped hollow organs. The cutting edge 470 of the knife 468, which is circular in configuration, cuts through the tissues of the hollow organs and into the annular cutting block 544, which is held within the anvil 530, as previously described. The driver tube 350 will travel whatever distance is necessary to bend the staples always into the same configuration. There is, of course, a maximum limit to tissue thickness which a specific staple length can accommodate as shown by marks 404 and 403. FIG. 22 depicts in phantom for the first embodiment the two concentric circular arrays of staples 159 which join together the ends of the hollow organ to be joined. The disclosure in FIG. 22 likewise applies to the second embodiment of the stapling instrument 310 and the cartridge 340. The excess portion of the ends of the hollow organ to be joined are severed by the action of knife edge 470. The vent holes 347 in anvil 530, and vent holes 349 formed in the body 510, as well as vent holes 451, 461 and 463 in the staple-carrying portion 344, allow for relief of gas, fluid or excess tissue trapped within the instrument on account of the procedure of stapling. The severed ends 300 and 302 of the hollow organ are retained around rod 352 and between the anvil-carrying part and the staple carrying part.

The next step in the procedure would be to rotate wing nut 360 to increase the spacing between the anvil-carrying part and the staple-carrying part to allow the stapled part of the hollow organ to be withdrawn from between these instrument parts and passed over the anvil-carrying part 346, so that the instrument may be withdrawn. To this end, the anvil carrying part 346 is provided with an external configuration typically of spherical dish-shape to facilitate the removal of the stapled organ from between the two parts 346 and 344 and passing of the stapled part of the organ over part 346.

The detailed discussion previously presented concerning the removal of the first embodiment of the instrument likewise applies to this embodiment of the instrument. The removal is best accomplished when the perimeter of the profile, in section through the axis as shown in FIG. 66, of the anvil-carrying part 346 is equal to or less than the circumference of the inner ring of staples represented by the inner circular array of spaced staple clinching grooves 532 in FIG. 67.

Although the present invention has been shown and described in terms of a preferred embodiment, it will be appreciated that various changes may be made without departing from the spirit of the concept.

What is claimed is:

1. A two-part disposable surgical stapling cartridge assembly for use with an actuator having first, second, and third relatively movable actuator members for stapling an annular pattern in hollow body organs, comprising:
(1) an anvil-carrying part including (a) a dish-shaped body, (b) an anvil having an annular array of staple-clinching grooves mounted in said dish-shaped body, and (c) first means for removably mounting said dish-shaped body on said first actuator member; and
(2) a staple-carrying part including (a) a staple guide body defining (i) an annular array of staple-holding grooves and (ii) second means for removably mounting said staple-carrying part on said second actuator member, said second means being the sole means associated with said cartridge assembly for retaining said staple-carrying part on said actuator, (b) a staple ejector means movably mounted in and permanently retained by said staple guide body and being contactable by said third actuator member when said staple guide body is mounted on said second actuator member for ejecting staples from said staple-holding grooves in response to actuation of said third actuator member, (c) annular knife means concentric with and inside said annular array of staple-holding grooves, said annular knife means being permanently mounted on said staple ejector means for movement with said staple ejector means for severing said hollow body organs inside the annular array of staples ejected from said staple-holding grooves, and (d) first and second mutually opposed and interfitting detent means respectively defined by said staple guide body and said ejector means for maintaining said staple ejector means and said annular knife means in a predetermined position in said staple guide body prior to mounting said staple-carrying part on said second actuator member and for preventing accidental relative movement of said staple guide body and said staple ejector means of the type which would cause ejection of the staples from said staple-holding grooves, said detent means being disengaged when said staple guide body is mounted on said second actuator member to allow said third actuator member to move said staple ejector means.

2. A two-part disposable surgical stapling cartridge assembly for use with an actuator having first, second, and third actuator members aligned with a first longitudinal axis and relatively movable parallel to said first longitudinal axis for stapling an annular pattern in body tissue, said cartridge assembly comprising:
(1) an anvil-carrying part including (a) a body, (b) an anvil mounted in said body and having an annular array of staple-clinching grooves, and (c) first means for removably mounting said body on a portion of said first actuator member which is located distally along said first longitudinal axis so that said staple-clinching grooves face in the proximal direction along said first longitudinal axis; and
(2) a staple-carrying part having a second longitudinal axis and including (a) staple guide body means having (i) an annular array of staple-holding grooves parallel to said second longitudinal axis and (ii) second means for removably mounting said staple-carrying part on a portion of said second actuator member which is proximal of said distally located portion of said first actuator member so that said first and second longitudinal axes are parallel and so that said staple-holding grooves face in the distal direction along said first longitudinal axis, said second means being the sole means associated with said cartridge assembly for retaining said staple-carrying part on said actuator when the anvil-carrying part is removed from the actuator, and (b) third means permanently retained by said staple guide body means and movable relative to said staple guide body means parallel to said second longitudinal axis, said third means including (i) fourth means for operatively relating said third means to said third actuator member when said staple-carrying part is mounted on said second actuator member so that said third means moves in the distal direction relative to said staple guide body means in response to distal motion of said third actuator member but so that said third means does not move in the proximal direction relative to said staple guide body means in response to proximal motion of said third actuator member, (ii) staple ejector means for ejecting staples from said staple-holding grooves when said third means moves distally relative to said staple guide body means in response to distal motion of said third actuator member, and (iii) annular knife means inside aaid annular array of staple-holding grooves for severing said body tissue inside the annular array of staples ejected from said staple-holding grooves when said third means moves distally relative to said staple guide body means in response to distal motion of said third actuator member.

3. The apparatus defined in claim 2 wherein said fourth means comprises a proximal-facing surface portion of said third means for abutting a distal-facing surface portion of said third actuator member when said staple-carrying part is mounted on said second actuator member, said abutting surface portions being the sole connection between said third means and said third actuator member.

4. The apparatus defined in claim 2 wherein said proximal-facing surface portion is the proximal-most surface of said third means, and wherein said distal-facing surface portion is the distal end of said third actuator member.

5. The apparatus defined in claim 2 wherein said fourth means is only capable of transmitting axial compression force between said abutting surface portions.

* * * * *